United States Patent
Long et al.

(10) Patent No.: US 11,938,263 B2
(45) Date of Patent: Mar. 26, 2024

(54) APPARATUSES, SYSTEMS, AND METHODS FOR PUMP CONTROL IN THERAPY DEVICES

(71) Applicant: KCI Licensing, Inc., San Antonio, TX (US)

(72) Inventors: Justin Alexander Long, Lago Vista, TX (US); Christopher Brian Locke, Bournemouth (GB); Thomas Alan Edwards, Hampshire (GB)

(73) Assignee: Solventum Intellectual Properties Company, Maplewood, MN (US)

( * ) Notice: Subject to any disclaimer, the term of this patent is extended or adjusted under 35 U.S.C. 154(b) by 0 days.

(21) Appl. No.: 17/636,233

(22) PCT Filed: Sep. 22, 2020

(86) PCT No.: PCT/IB2020/058840
§ 371 (c)(1),
(2) Date: Feb. 17, 2022

(87) PCT Pub. No.: WO2021/059127
PCT Pub. Date: Apr. 1, 2021

(65) Prior Publication Data
US 2022/0339343 A1 Oct. 27, 2022

Related U.S. Application Data

(60) Provisional application No. 62/904,911, filed on Sep. 24, 2019.

(51) Int. Cl.
*A61M 1/00* (2006.01)
(52) U.S. Cl.
CPC ............... *A61M 1/74* (2021.05); *A61M 1/85* (2021.05); *A61M 1/96* (2021.05); *A61M 1/912* (2021.05);
(Continued)

(58) Field of Classification Search
CPC ............ A61M 1/74; A61M 1/85; A61M 1/96; A61M 1/912; A61M 1/94;
(Continued)

(56) References Cited

U.S. PATENT DOCUMENTS 1,355,846 A  10/1920  Rannells
2,547,758 A   4/1951  Keeling
(Continued)

FOREIGN PATENT DOCUMENTS

AU  550575 B2  3/1986
AU  745271 B2  3/2002
(Continued)

OTHER PUBLICATIONS

International Search Report and Written Opinion for corresponding Application No. PCT/IB2020/058840 dated Feb. 8, 2021.
(Continued)

*Primary Examiner* — Nicholas J. Weiss
*Assistant Examiner* — Brandon W. Levy

(57) ABSTRACT

This disclosure describes devices, systems, and methods related to therapy devices including pumps that are operable in multiple operating modes. An exemplary wound therapy device includes a pump configured to be worn by a user and a controller coupled to the pump and configured to transition the pump from operating in a first operating mode to operating in a second operating mode responsive to a pressure of the wound therapy device satisfying a first pressure threshold. The first operating mode is associated with a first drive voltage that is different from a second drive voltage associated with the second operating mode.

20 Claims, 10 Drawing Sheets

(52) U.S. Cl.
CPC ....... *A61M 1/94* (2021.05); *A61M 2205/0294* (2013.01); *A61M 2205/3331* (2013.01)

(58) Field of Classification Search
CPC .. A61M 2205/0294; A61M 2205/3331; A61M 1/984; A61M 1/966; A61M 2205/15; A61M 2205/3344; A61M 2205/3576; A61M 2205/42; A61M 2205/50; A61M 2205/587; A61M 2205/8212; A61M 2209/088; A61M 2205/3334; A61M 1/80; A61M 1/918; A61M 1/71; A61M 2205/18; A61M 1/00; A61M 2205/3365; A61M 2205/14; A61M 1/916; A61M 1/732; A61M 1/60; A61M 27/00; A61M 3/022; A61F 13/00068

See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2011/0178451 A1* | 7/2011 | Robinson ............ B29C 44/5636 264/237 |
| 2012/0271256 A1 | 10/2012 | Locke et al. |
| 2013/0267917 A1* | 10/2013 | Pan ........................ A61M 1/96 604/319 |
| 2014/0163491 A1 | 6/2014 | Schuessler et al. |
| 2015/0080788 A1 | 3/2015 | Blott et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |

(56) References Cited

FOREIGN PATENT DOCUMENTS

| | | |
|---|---|---|
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2013015827 A2 | 1/2013 |
| WO | WO-2013064852 A1 * | 5/2013 ........... A61M 1/0031 |
| WO | WO-2018017391 A1 * | 1/2018 ....... A61F 13/00068 |
| WO | WO-2018164803 A1 * | 9/2018 .............. A61M 1/73 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., JR., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, YU. A., et al; "Vacuum Therapy in the Treatment of Purulent Lactation Mastitis"; Vestnik Khirurgi, May 14, 1986, pp. 66-70, and 9 page English translation thereof.
Yusupov. YU.N., et al; "Active Wound Drainage", Vestnki Khirurgi, vol. 138, Issue 4, 1987, and 7 page English translation thereof.
Davydov, YU.A., et al; "Bacteriological and Cytological Assessment of Vacuum Therapy for Purulent Wounds"; Vestnik Khirugi, Oct. 1988, pp. 48-52, and 8 page English translation thereof.
Davydov, YU.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax,"Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract,

(56) References Cited

OTHER PUBLICATIONS editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

* cited by examiner

APPARATUSES, SYSTEMS, AND METHODS FOR PUMP CONTROL IN THERAPY DEVICES

CROSS-REFERENCE TO RELATED APPLICATIONS

This application claims the benefit of priority to U.S. Provisional Application No. 62/904,911, filed on Sep. 24, 2019, which is incorporated herein by reference in its entirety.

TECHNICAL FIELD

Aspects of the present disclosure relate generally to a wound therapy devices, and more specifically, but not by way of limitation, to wound therapy devices that provide pressurized wound therapy.

BACKGROUND

Some therapy devices provide therapeutic pressure to a wound site of a user. For example, these therapy devices can include a dressing coupled to the wound site and a pump that applies a therapeutic amount of positive or negative pressure to the wound site. Most such therapy devices are large bulky devices not designed for mobile or discreet use. Some mobile and discreet therapy devices are small enough to be discreetly worn by the user. Such discreet therapy devices may include small, rechargeable batteries to power the therapy device and enable use of the therapy device continuously throughout the day. However, while the therapy device can be made small enough to be discreetly and comfortably worn, the pumps of the therapy device generate some audible noise. Accordingly, while such therapy devices are discreet to the eye, such systems produce noise and are not discreet in terms of sound. As an example, diaphragm pumps generate an audible noise, e.g., an audible "hum" of low frequency noise.

Some of the pumps used in therapy devices are not very efficient in terms of power and therefore battery consumption. For example, under normal conditions, the batteries may be sufficient to power the discreet therapy devices using a diaphragm pump for 12 to 18 hours before needing to be replaced or recharged. However, this time can be significantly decreased if there is an air leak. The time can also be decreased based on temperature, battery degradation, and if the batteries have not been fully recharged. Thus, a user may end up in a situation where they are unable to recharge the battery, for example because they are away from home, but the battery is low on charge and/or rapidly depleting, such as due to a leak in a seal of the dressing. If the battery becomes depleted, the therapy device no longer functions and no longer provides therapeutic pressure to the wound site. Additionally, or alternatively, the pumps may not be efficient at quickly reaching a therapeutic pressure (e.g., due to the small amount of voltage provided by the batteries), and thus may not reach a therapeutic pressure when powered on for multiple minutes.

SUMMARY

This disclosure describes apparatus, systems, methods, and computer-readable storage devices for controlling a pump of a therapy device (e.g., a wound therapy device) in multiple operating modes, i.e., two or more operating modes. For example, a controller (e.g., a processor or other hardware) of a therapy device may be configured to operate the pump in one of at least three operating modes: a first operating mode (e.g., a "boost operating mode"), a second operating mode (e.g., a "normal power operating mode"), and a third operating mode (e.g., a "reduced power operating mode"). Each of the different operating modes may provide respective benefits, and being able to operate the pump in the different operating modes improves the flexibility of the pump, as compared conventional pumps that are only configured to operate in a single operating mode.

Additionally, the use of two or more of the multiple operating modes may enable power savings and use of silent pumps in disposable (e.g., single use) and/or discreet therapy systems. To illustrate, such therapy devices may enable the use of silent pumps which are more power inefficient as compared to conventional pumps, such as diaphragm style pumps, used in discreet therapy systems. As an illustrative example, piezoelectric pumps are inaudible (or substantially inaudible) and may be used. To illustrate, piezoelectric pumps generate a high frequency noise that is above the range of frequencies that humans can hear. Accordingly, such piezoelectric pumps operate silently and can be used to discreetly provide pressure therapy. The generated power savings of the multiple modes can enable silent pumps, such as piezoelectric pumps which are more power inefficient as compared to conventional diaphragm style pumps, to be used in discreet therapy systems and to provide all day power (e.g., 12-18 hours). In addition, the multiple modes may enable a leaking dressing or system to continue with partial functionality for a longer period of time as compared to conventional systems, which when faced with a leaking dressing, would consume more power while partially functioning and would cease operating all together in a shorter period of time.

The boost operating mode may be used to cause the pump to more quickly generate a therapeutic level of pressure (e.g., starting from ambient pressure). To achieve the quicker time, the boost operating mode is associated with a drive voltage that is different from the other operating modes. For example, a drive voltage provided to the pump in the boost operating mode may be greater than a drive voltage provided to the pump in the normal power operating mode or the reduced power operating mode. Because a greater amount of drive voltage is provided in the boost operating mode, the boost operating mode generates a higher output pressure and work and may discharge the batteries of the therapy device more quickly, as compared to the normal power operating mode. Thus, the boost operating mode is used for a limited amount of time. For example, the controller may operate the pump in the boost operating mode from when the therapy device is powered on until a particular target pressure (e.g., a therapeutic pressure level) is output by the pump. Thus, the boost operating mode may reduce an amount of time from power-on until the pump is generating a particular target pressure. Additionally, the increased power used in the boost operating mode may be offset by the reduced amount of time used to reach the particular target pressure.

The normal power operating mode may be used in normal operating conditions (e.g., when there is no leak and when the battery is sufficiently charged). For example, after reaching the particular target pressure during operation in the boost operating mode, the controller may transition the pump from the boost operating mode to the normal power operating mode. Alternatively, the normal power operating mode may be a default mode that is used upon startup. In implementations that have a boost operating mode, the normal power operating mode may have a lower drive voltage than the boost operating mode. Thus, the normal power operating mode preserves battery life as compared to the boost operating mode. The controller may continue to operate the pump in the normal power operating mode until therapy is discontinued. In some implementations, the controller may identify a particular condition, such as a leak condition, a low battery condition, or both, and transition the pump into another (e.g., non-normal operating condition) operating mode.

For example, if a leak condition or a low battery condition is detected, the controller transitions the pump into a reduced power operating mode (e.g., from the boost operating mode or from the normal power operating mode). In some implementations, a leak condition may be detected if a leak counter satisfies a threshold, and the leak counter is incremented when a pressure output by the pump is less than a target pressure, as further described herein. A low battery condition may be detected when a battery level of one or more batteries of the therapy device is less than a particular target % (e.g., a target battery level or threshold) or when a removable (and rechargeable) battery is disconnected from the therapy device.

The reduced power operating mode may be associated with a duty cycle range of the pump that is different from a duty cycle range of the pump in the normal power operating mode. As used herein, a duty cycle of the pump refers to a percentage of time that the pump is turned on compared to the pump being off (e.g., inactive or stationary) during a particular time period. For example, during operation in the normal power operating mode, the pump may be on for 70% of a particular time period, while during operation in the reduced power operating mode, the pump may be on for 40% of the particular time period. The duty cycle may be adjusted or set by decreasing an on-time or run interval, increasing an off-time or downtime interval, or a combination thereof.

Having a different (e.g., lower) duty cycle causes the pump to consume a different (e.g., reduced) amount of power. To illustrate, the pump still pulls (is provided with) the same voltage and current when on (e.g., same instantaneous power), but the reduced on time reduces the amount of power of a time period (e.g. average power). Because the duty cycle is different (e.g., less) than in the normal power operating mode, the reduced power operating mode uses less average power than the normal power operating mode, thereby conserving battery charge as compared to the normal power operating mode.

Additionally, reducing a duty cycle may also affect an amount of pressure in the dressing. For example, at reduced duty cycles (and possibly with a small leak) the pressure of the dressing may be lower (i.e., closer to ambient, and thus for negative pressure therapy the pressure will be larger). As another example, at reduced duty cycles (and possibly with a small leak) the pressure of the dressing may fluctuate more than at a normal duty cycle. To illustrate, as the pump outputs at a continuous rate while on (at a given voltage), less on-time may generate less of an average pressure differential in the dressing and/or produce a larger range of pressures in the reduced power operating mode. However, the reduced power operating mode is designed such that the lower amount of pressure is still a therapeutic amount of pressure (e.g., between 50 and 200 millimeters of mercury (mm Hg)). Thus, the therapy device may operate longer than conventional therapy devices, which gives the user more chance to fix the leak or two recharge the battery. If the leak condition or the low battery condition are solved, the controller transitions the pump back into the normal operating mode.

Alternatively, a leak mode may have an increased duty cycle as compared to the normal operating mode. For example, a duty cycle may be increased to overcome a small leak based on one or more conditions, such as when battery power is high, time of day is late, and/or based on user input. To illustrate, the power may run continuously (100% duty cycle) or have longer on-time cycles or limits and/or shorter off-time limits to overcome a small leak, i.e., remain within a target operating pressure.

Thus, the present disclosure describes a controller that is configured to operate a pump of a therapy device in multiple operating modes. The multiple operating modes may include a normal power operating mode and one or more boost operating modes, one or more reduced power operating modes, or a combination thereof. As an illustrative example, the controller may transition the pump between two modes, normal and low power modes. To illustrate, the controller may transition the pump from the normal power operating mode to the reduced power operating mode when a leak condition or a low battery condition is detected. Once the leak is fixed (e.g., by manual intervention) or the battery level is greater than the target battery level, the controller returns the pump to the previous operating mode. The controller may determine that the leak is fixed based on a seal counter satisfying a threshold or user input.

As another illustrative example, the controller may transition the pump into the boost operating mode upon power-on and may transition the pump from the boost operating mode to the normal operating mode when a particular pressure output is reached by the pump. The controller may transition the pump from the normal power operating mode (or the boost operating mode) to the reduced power operating mode when a leak condition or a low battery condition is detected. Once the leak is fixed (e.g., by manual intervention) or the battery level is greater than the target battery level, the controller returns the pump to the previous operating mode. The controller may determine that the leak is fixed based on a seal counter satisfying a threshold or user input.

Some embodiments of the present wound therapy devices comprise: a pump configured to be worn by a user, and a controller coupled to the pump and configured to transition the pump from operating in a first operating mode to operating in a second operating mode responsive to a pressure of the wound therapy device satisfying a first pressure threshold. The first operating mode is associated with a first drive voltage that is different from a second drive voltage associated with the second operating mode.

In some of the foregoing embodiments of the present wound therapy devices, the first drive voltage is greater than the second drive voltage. Additionally, or alternatively, the pump comprises a piezoelectric pump. In some such embodiments, the pump is substantially inaudible to a human ear. In some such implementations, the pump is configured to operate at frequencies above substantially 10 kilohertz.

In some of the foregoing embodiments, the present wound therapy devices further comprise a pressure sensor coupled to the pump and configured to measure the pressure output by the pump and to send pressure data to the controller, the pressure data indicative of the pressure. Additionally, or alternatively, the present wound therapy devices may further comprise a pressure sensor coupled to a dressing configured to be coupled to a wound site. The pressure sensor is configured to measure the pressure at the dressing and to send pressure data to the controller, the pressure data indicative of the pressure.

In some of the foregoing embodiments of the present wound therapy devices, the pump is configured to apply a negative pressure. Alternatively, the pump may be configured to apply a positive pressure. Additionally, or alternatively, the first drive voltage is substantially 18 volts, and the second drive voltage is substantially 15 volts.

In some of the foregoing embodiments of the present wound therapy devices, the controller is further configured to, responsive to the pressure failing to satisfy the first pressure threshold, determine whether a time elapsed since entering the first operating mode satisfies a time threshold and, responsive to the time failing to satisfy the time threshold, continue to operate the pump in the first operating mode. In some such embodiments, the controller is further configured to, responsive to the time satisfying the time threshold, increment a leak counter, determine whether the leak counter satisfies a leak threshold, and, responsive to determining that the leak counter satisfies the leak threshold, initiate a leak alert and operate the pump in a third operating mode. The second operating mode is associated with a first duty cycle range of the pump and the third operating mode is associated with a second duty cycle range of the pump that is different from the first duty cycle range. In some such embodiments, the pump comprises one or more indicators and initiating the leak alert comprises activating one of the one or more indicators. In some such embodiments, the one or more indicators comprise one or more lights. Additionally, or alternatively, the controller is configured to initiate the leak alert by initiating transmission of a leak alert message to a mobile device associated with the user.

In some of the foregoing embodiments of the present wound therapy devices, the wound therapy devices further comprise a battery, and the controller is further configured to, responsive to determining that the leak counter fails to satisfy the leak threshold, determine whether a battery level of the battery satisfies a battery threshold and, responsive to determining that the battery level satisfies the battery threshold, continue to operate the pump in the first operating mode. In some such embodiments, the controller is further configured to, responsive to determining that the battery level fails to satisfy the battery threshold, initiate a low battery alert and operate the pump in a third operating mode. The second operating mode is associated with a first duty cycle range and the third operating mode is associated with a second duty cycle range that is different from the first duty cycle range. In some such embodiments, the pump comprises one or more indicators and initiating the low battery alert comprises activating one of the one or more indicators. Additionally, or alternatively, the controller is configured to initiate the low battery alert by initiating transmission of a low battery alert message to a mobile device associated with the user.

Some embodiments of the present methods comprise: identifying a power-on event of a wound therapy device, the wound therapy device configured to be worn by a user, responsive to the power-on event, operating a pump of the wound therapy device in a first operating mode, the first operating mode associated with a first drive voltage, receiving, from a pressure sensor of the wound therapy device, pressure data indicating a pressure applied by the pump, determining whether the pressure satisfies a pressure threshold, and, responsive to determining that the pressure satisfies the first pressure threshold, operating the pump in a second operating mode. The second operation mode is associated with a second drive voltage, and the first drive voltage is greater than the second drive voltage.

In some of the foregoing embodiments of the present methods, operating the pump in the first operating mode comprises sending one or more control signals indicating the first operating mode to the pump. In some of the foregoing embodiments of the present methods, the methods further comprise receiving, from a pressure sensor, second pressure data indicating a second pressure applied by the pump, comparing the second pressure to a second pressure threshold, and, responsive to determining that the second pressure is greater than the second pressure threshold, reducing a duty cycle of the pump. In some such embodiments, the present methods further comprise determining whether a battery level of the wound therapy device satisfies a battery threshold, and, responsive to the battery level satisfying the battery threshold, continuing to operate the pump in the second operating mode. In some such embodiments, the present methods further comprise, responsive to the battery level failing to satisfy the battery threshold: initiating a low battery alert and operating the pump in a third operating mode. The second operating mode is associated with a first duty cycle range of the pump, and the third operating mode is associated with a second duty cycle range of the pump that is different from the first duty cycle range.

In some of the foregoing embodiments of the present methods, the methods further comprise, responsive to determining that the second pressure is substantially equal to the second pressure threshold, maintaining a duty cycle of the pump. In some such embodiments, the present methods also comprise continuing to operate the pump in the second operating mode.

In some of the foregoing embodiments of the present methods, the present methods further comprise, responsive to determining that the second pressure is less than the second pressure threshold, determining whether a time since entering the second operating mode satisfies a time threshold, and, responsive to determining that the time does not satisfy the time threshold, increasing a duty cycle of the pump. The present methods may also comprise continuing to operate the pump in the second operating mode. In some such embodiments, the present methods also comprise, responsive to determining that the time satisfies the time threshold, incrementing a leak counter a determining whether the leak counter satisfies a leak threshold. In some such embodiments, the present methods further comprise, responsive to determining that the leak counter does not satisfy the leak threshold, increasing the duty cycle of the pump and continuing to operate the pump in the second operating mode. In some such embodiments, the present methods further comprise, responsive to determining that the leak counter satisfies the leak threshold: initiating a leak alert, and operating the pump in a third operating mode. The second operating mode is associated with a first duty cycle range of the pump, and the third operating mode is associated with a second duty cycle range of the pump that is different from the first duty cycle range.

Some embodiments of the present wound therapy devices comprise: a pump configured to be worn by a user and a controller coupled to the pump and configured to operate the pump in one of at least three operating modes. A first operating mode of the at least three operating modes is associated with a first drive voltage, a second operating mode of the at least three operating modes is associated with a second drive voltage and a first duty cycle range of the pump, the second drive voltage different from the first drive voltage, and a third operating mode of the at least three operating modes is associated with a second duty cycle range of the pump, the second duty cycle range different from the first duty cycle range.

In some of the foregoing embodiments of the present wound therapy devices, the controller is further configured to operate the pump in the first operating mode responsive to detecting a power-on condition. Additionally, or alternatively, the controller is further configured to transition the pump from the first operating mode to the second operating mode responsive to a determination that a pressure applied by the pump satisfies a first pressure threshold. Additionally, or alternatively, the controller is further configured to transition the pump from the first operating mode or the second operating mode to the third operating mode based on a leak counter satisfying a leak threshold. In some such embodiments, the third operating mode corresponds to a leak alert mode.

In some of the foregoing embodiments of the present wound therapy devices, the present wound therapy devices further comprise a battery, and the controller is further configured to transition the pump from the first operating mode or the second operating mode to the third operating mode based on a battery level of the battery failing to satisfy a battery threshold. In some such embodiments, the third operating mode corresponds to a low battery alert mode. Additionally, or alternatively, the present wound therapy devices further comprise a first battery, and the controller is further configured to transition the pump from the first operating mode or the second operating mode to the third operating mode responsive to detecting that a second battery is not connected. Additionally, or alternatively, the at least three operating modes include a fourth operating mode associated with a third duty cycle range of the pump, the third duty cycle range different from the first duty cycle range. In such embodiments, the third operating mode corresponds to a leak alert mode, and the fourth operating mode corresponds to a low battery alert mode.

Some embodiments of the present methods comprise: operating a pump of a wound therapy device in a first operating mode, the first operating mode associated with a first duty cycle range of the pump, determining whether a leak counter satisfies a leak counter threshold, and, responsive to determining that the leak counter satisfies the leak counter threshold, operating the pump in a second operating mode. The second operating mode is associated with a second duty cycle range of the pump that is different from the first duty cycle range.

In some of the foregoing embodiments of the present methods, the second duty cycle range is less than the first duty cycle range. In some of the foregoing embodiments of the present methods, the methods further comprise receiving, from a pressure sensor, pressure data indicating a pressure applied by the pump and determining whether the pressure is greater than a pressure threshold. In some such embodiments, the present methods also comprise, responsive to determining that the pressure is greater than the pressure threshold, reducing a duty cycle of the pump and incrementing a seal counter. In some such embodiments, the present methods further comprise determining whether the seal counter satisfies a seal threshold and, responsive to the seal counter failing to satisfy the seal threshold, initiating a leak alert and continuing to operate the pump in the second operating mode. In some such embodiments, the present methods further comprise, responsive to the seal counter satisfying the seal threshold, determining whether a battery level of one or more batteries of the wound therapy device satisfies a battery threshold and, responsive to the battery level satisfying the battery threshold, operating the pump in the first operating mode. In some such embodiments, the present methods further comprise, responsive to the battery level failing to satisfy the battery threshold, initiating a low battery alert and continuing to operate the pump in the second operating mode.

In some of the foregoing embodiments of the present methods, the present methods further comprise, responsive to determining that the pressure is equal than the pressure threshold, maintaining a duty cycle of the pump and incrementing a seal counter. The present methods may also comprise, responsive to determining that the pressure is less than the pressure threshold, determining whether a time since entry of the second operating mode satisfies a time threshold and, responsive to determining that the time fails to satisfy the time threshold, initiating a leak alert and continuing to operate the pump in the second operating mode. In some such embodiments, the present methods further comprise, responsive to determining that the time satisfies the time threshold: increasing a duty cycle of the pump, initiating the leak alert, and continuing to operate the pump in the second operating mode.

Some embodiments of the present computer-readable storage devices store instructions that, when executed by a processor, cause a processor to perform operations for wound therapy, the operations comprising: identifying a power-on event of a wound therapy device, the wound therapy device configured to be worn by a user, responsive to the power-on event, operating a pump of the wound therapy device in a first operating mode, the first operating mode associated with a first drive voltage, receiving, from a pressure sensor, pressure data indicating a pressure applied by the pump, responsive to determining that the pressure satisfies the first pressure threshold, operating the pump in a second operating mode, the second operating mode associated with a second drive voltage and a first duty cycle range, wherein the first drive voltage is greater than the second drive voltage, determining whether a battery level of one or more batteries of the wound therapy device satisfies a battery threshold or whether a leak counter satisfies a leak threshold, and, responsive to determining that the battery level fails to satisfy the battery threshold or that the leak counter satisfies the leak threshold, operating the pump in a third operating mode. The third operating mode is associated with a second duty cycle range that is less than the first duty cycle range Some embodiments of the present systems comprise: a wound device configured to be worn by a user. The wound therapy device comprises: a pump and a controller coupled to the pump. The controller is configured to operate the pump in one of three operating modes. A first operating mode of the three operating modes is associated with a first drive voltage, a second operating mode of the three operating modes is associated with a second drive voltage and a first duty cycle range, the second drive voltage different from the first drive voltage, and a third operating mode of the three operating modes is associated with a second duty cycle range, the second duty cycle range different from the first duty cycle range. The present kits also comprise a dressing configured to be coupled to a wound site and to the wound therapy device.

In some of the foregoing embodiments of the present systems, the systems further comprise a tube configured to couple the pump to the dressing. Additionally, or alternatively, the systems further comprise a first battery configured to power the wound therapy device. In some such embodiments, the systems further comprise a second battery configured to power the wound therapy device.

Some embodiments of the present wound therapy devices comprise: a pump configured to be worn by a user and a controller coupled to the pump and configured to transition the pump from operating in a first operating mode to operating in a second operating mode responsive to determining a leak counter satisfies a threshold or a battery level satisfies a battery level threshold. The first operating mode is associated with a first duty cycle range that is different from a second duty cycle range associated with the second operating mode.

In some of the foregoing embodiments of the present wound therapy devices, the first duty cycle range is greater than the second duty cycle range. In some of the foregoing embodiments of the present wound therapy devices, the controller is further configured to reduce a duty cycle of the pump from within the first duty cycle range to within the second duty cycle range responsive to transitioning the pump from operating in the first operating mode to the second operating mode. In some such embodiments, the controller is configured to reduce the duty cycle by decreasing a maximum on-time of a time period. Additionally, or alternatively, the controller is configured to reduce the duty cycle by increasing a maximum off-time of a time period. Additionally, or alternatively, the controller is configured to reduce the duty cycle by reducing a number of off-to-on cycles of a time period.

As used herein, various terminology is for the purpose of describing particular implementations only and is not intended to be limiting of implementations. For example, as used herein, an ordinal term (e.g., "first," "second," "third," etc.) used to modify an element, such as a structure, a component, an operation, etc., does not by itself indicate any priority or order of the element with respect to another element, but rather merely distinguishes the element from another element having a same name (but for use of the ordinal term). The term "coupled" is defined as connected, although not necessarily directly, and not necessarily mechanically. Additionally, two items that are "coupled" may be unitary with each other. To illustrate, components may be coupled by virtue of physical proximity, being integral to a single structure, or being formed from the same piece of material. Coupling may also include mechanical, thermal, electrical, communicational (e.g., wired or wireless), or chemical coupling (such as a chemical bond) in some contexts.

The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. As used herein, the term "approximately" may be substituted with "within 10 percent of" what is specified. Additionally, the term "substantially" may be substituted with "within [a percentage] of" what is specified, where the percentage includes 0.1, 1, or 5 percent; or may be understood to mean with a design, manufacture, or measurement tolerance. The phrase "and/or" means and or. To illustrate, A, B, and/or C includes: A alone, B alone, C alone, a combination of A and B, a combination of A and C, a combination of B and C, or a combination of A, B, and C. In other words, "and/or" operates as an inclusive or. Similarly, the phrase "A, B, C, or a combination thereof" or "A, B, C, or any combination thereof" includes: A alone, B alone, C alone, a combination of A and B, a combination of A and C, a combination of B and C, or a combination of A, B, and C.

The terms "comprise" (and any form of comprise, such as "comprises" and "comprising"), "have" (and any form of have, such as "has" and "having"), and "include" (and any form of include, such as "includes" and "including"). As a result, an apparatus that "comprises," "has," or "includes" one or more elements possesses those one or more elements, but is not limited to possessing only those one or more elements. Likewise, a method that "comprises," "has," or "includes" one or more steps possesses those one or more steps, but is not limited to possessing only those one or more steps.

Any aspect of any of the systems, methods, and article of manufacture can consist of or consist essentially of— rather than comprise/have/include—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb. Additionally, it will be understood that the term "wherein" may be used interchangeably with "where."

Further, a device or system that is configured in a certain way is configured in at least that way, but it can also be configured in other ways than those specifically described. The feature or features of one embodiment may be applied to other embodiments, even though not described or illustrated, unless expressly prohibited by this disclosure or the nature of the embodiments.

Some details associated with the aspects of the present disclosure are described above, and others are described below. Other implementations, advantages, and features of the present disclosure will become apparent after review of the entire application, including the following sections: Brief Description of the Drawings, Detailed Description, and the Claims.

BRIEF DESCRIPTION OF THE DRAWINGS

A further understanding of the nature and advantages of the present disclosure may be realized by reference to the following drawings. The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

DETAILED DESCRIPTION

Figure 1:
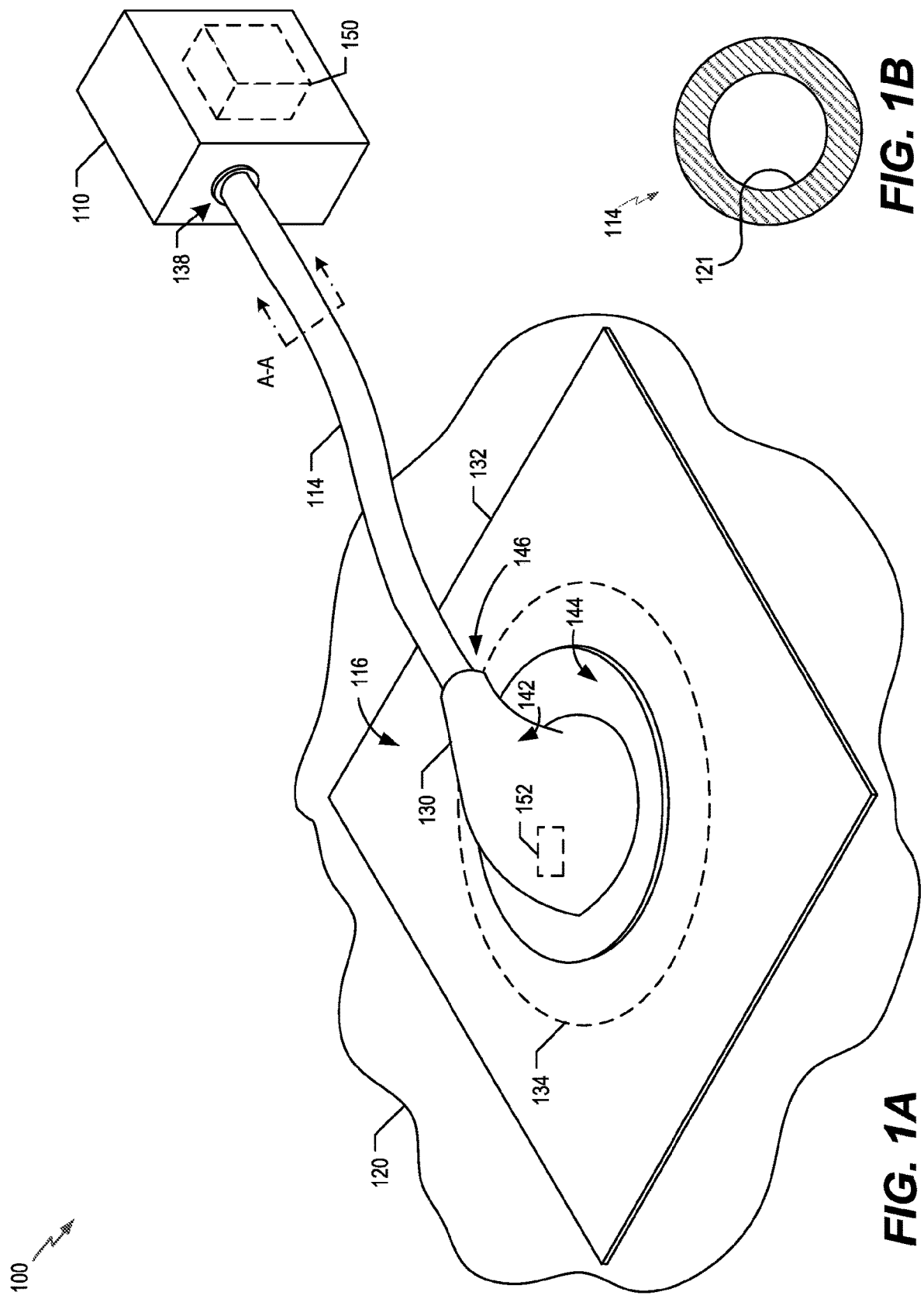
FIG. 1A is a diagram of an example of a therapy system for pressurized wound therapy.
FIG. 1B is a diagram of an example of a tube taken along line A-A of FIG. 1A.

As used herein, the terms "tissue site" and "target tissue" as used herein can broadly refer to a wound (e.g., open or closed), a tissue disorder, and/or the like located on or within tissue, such as, for example, bone tissue, adipose tissue, muscle tissue, neural tissue, dermal tissue, vascular tissue, connective tissue, cartilage, tendons, ligaments, and/or the like. The terms "tissue site" and "target tissue" as used herein can also refer to a surrounding tissue area(s) and/or areas of tissue that are not necessarily wounded or exhibit a disorder, but include tissue that would benefit from tissue generation and/or tissue that may be harvested and transplanted to another tissue location. The terms "tissue site" and "target tissue" may also include incisions, such as a surgical incision. In some implementations, "target tissue" may correspond or refer to a wound, and "tissue site" may correspond or refer to a tissue area(s) surrounding and including the target tissue. Additionally, the term "wound" as used herein can refer to a chronic, subacute, acute, traumatic, and/or dehisced incision, laceration, puncture, avulsion, and/or the like, a partial-thickness and/or full thickness burn, an ulcer (e.g., diabetic, pressure, venous, and/or the like), flap, and/or graft. A wound may include chronic, acute, traumatic, subacute, and dehisced wounds, partial-thickness burns, ulcers (such as diabetic, pressure, or venous insufficiency ulcers), flaps, grafts, and fistulas, for example.

The term "positive-pressure" (or "hyperbaric") as used herein generally refers to a pressure greater than a local ambient pressure, such as the ambient pressure in a local environment external to a sealed therapeutic environment (e.g., an internal volume). In most cases, this positive-pressure will be greater than the atmospheric pressure at which the patient is located. Alternatively, the positive-pressure may be greater than a hydrostatic pressure associated with tissue at the tissue site. Unless otherwise indicated, values of pressure stated herein are gauge pressures. References to increases in positive-pressure typically refer to an increase in absolute pressure, and decreases in positive-pressure typically refer to a decrease in absolute pressure. Additionally, the process of increasing pressure may be described illustratively herein as "applying", "delivering," "distributing," "generating", or "providing" positive-pressure, for example.

The term "reduced-pressure" (and "negative-pressure" or "hypobaric") as used herein generally refers to a pressure less than a local ambient pressure, such as the ambient pressure in a local environment external to a sealed therapeutic environment (e.g., an internal volume). In most cases, this reduced-pressure will be less than the atmospheric pressure at which the patient is located. Alternatively, the reduced-pressure may be less than a hydrostatic pressure associated with tissue at the tissue site. Unless otherwise indicated, values of pressure stated herein are gauge pressures. References to increases in reduced-pressure typically refer to a decrease in absolute pressure, and decreases in reduced-pressure typically refer to an increase in absolute pressure. Additionally, the process of reducing pressure may be described illustratively herein as "applying", "delivering," "distributing," "generating", or "providing" reduced-pressure, for example.

The term "fluid" may refer to liquid, gas, air, or a combination thereof. The term "fluid seal," or "seal," means a seal adequate to maintain a pressure differential (e.g., positive-pressure or reduced-pressure) at a desired site given the particular pressure source or subsystem involved. Similarly, it may be convenient to describe certain features in terms of fluid "inlet" or "outlet" in such a frame of reference. However, the fluid path may also be reversed in some applications, such as by substituting a reduced-pressure source (negative or hypobaric pressure source) for a positive-pressure source, and this descriptive convention should not be construed as a limiting convention.

FIG. 1A shows a perspective view of an illustrative system 100 (e.g., a therapy system) for providing wound therapy. System 100 may include a therapy device 110, a tube 114, and a dressing 116. System 100 is configured to provide therapy (e.g., oxygen therapy, positive-pressure therapy, negative-pressure therapy, or a combination thereof) at a tissue site 120 associated with a target area of a patient. For example, dressing 116 may be in fluid communication with tissue site 120 and may be in fluid communication with therapy device 110 via tube 114. In some implementations, system 100 may include one or more components commercially available through and/or from KCI USA, Inc. of San Antonio, Tex., U.S.A., and/or its subsidiary and related companies (collectively, "KCI"). In some implementations, system 100 is a disposable and/or discreet therapy system. For example, the therapy system is sized to fit underneath clothing and/or to attach to clothing of a person. An illustrative, non-limiting example of commercially available discreet therapy systems include a "V.A.C. VIA"™ Therapy System available from Kinetic Concepts, Inc. (KCI) of San Antonio, Tex.

Therapy device 110 (e.g., a treatment apparatus) is configured to provide therapy to tissue site 120 via tube 114 and dressing 116. For example, therapy device 110 may include a pressure source (e.g., a negative-pressure source, such as a pump, or a positive-pressure source, such as a pressurized oxygen container, an oxygen concentrator, or an oxygen collector) configured to be actuatable (and/or actuated) to apply pressure differential relative to ambient conditions to dressing 116. As illustrative, non-limiting examples, positive-pressure applied to a tissue site may typically ranges between 5 millimeters mercury (mm Hg) (667 pascals (Pa)) and 30 mm Hg (4.00 kilo (k) Pa). Common therapeutic ranges are between 10 mm Hg (1.33 kPa) and 25 mm Hg (3.33 kPa). As illustrative, non-limiting examples, reduced-pressure applied to a tissue site may typically ranges between −5 millimeters mercury (mm Hg) (−667 pascals (Pa)) and −500 mm Hg (−66.7 kilo (k) Pa). Common therapeutic ranges are between −75 mm Hg (−9.9 kPa) and −300 mm Hg (−39.9 kPa).

Figure 2:
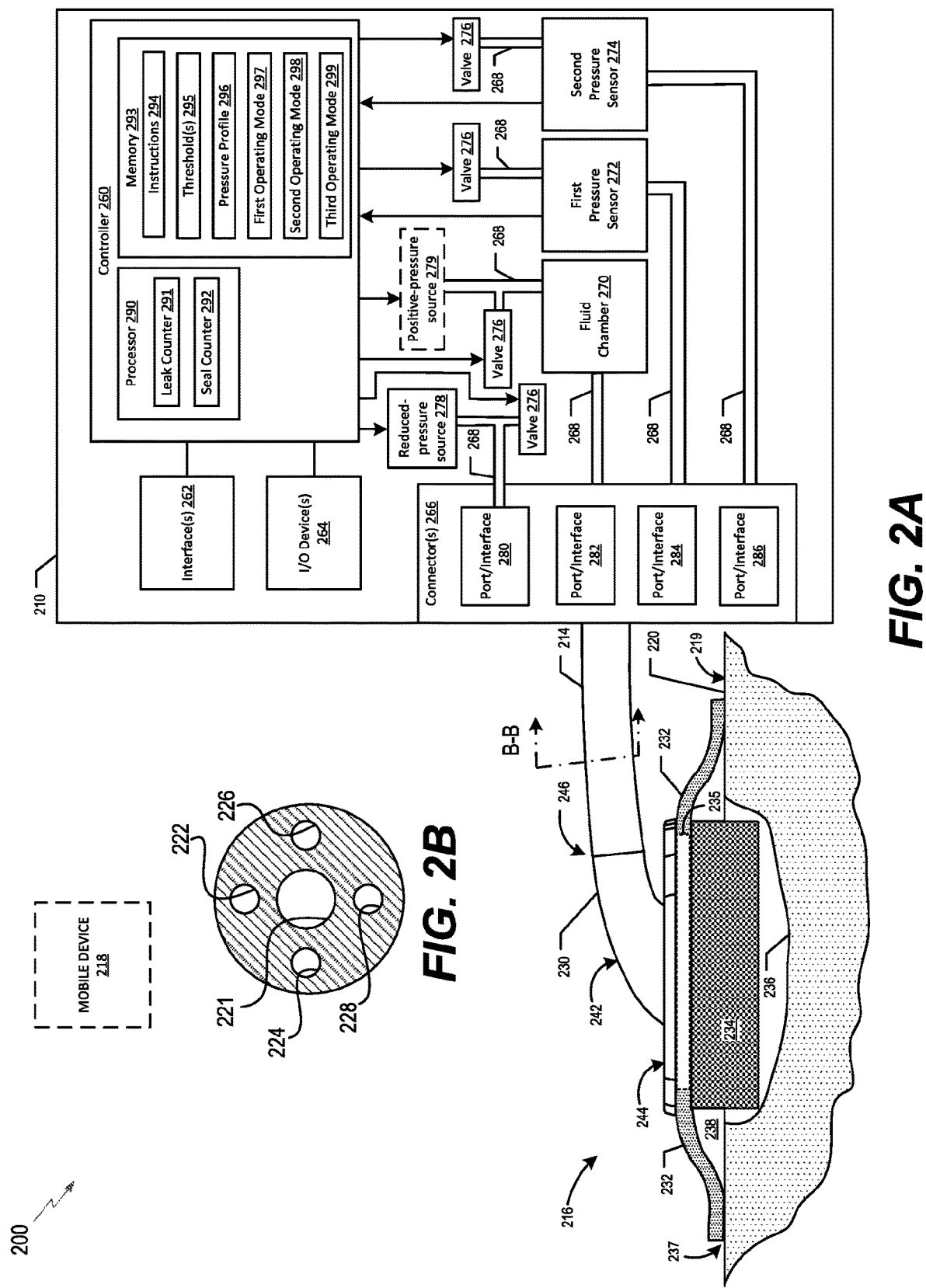
FIG. 2A is a diagram of an example of another system for wound therapy.
FIG. 2B is a cross-sectional view of an example of a tube taken along line B-B of FIG. 2A.

In some implementations, as described further with reference to FIG. 2A, the therapy device 110 includes a reduced-pressure source, such as a vacuum source (e.g., a pump and/or the like), configured to be actuatable (and/or actuated) to apply reduced-pressure (e.g., negative pressure) to dressing 116. In some implementations, therapy device 110 may alternate between providing positive-pressure therapy and negative-pressure therapy to the dressing 116, may provide positive-pressure therapy to a first portion of the dressing 116 and negative-pressure therapy to a second portion of the dressing 116, may provide no positive or negative pressure, or a combination thereof. In some such implementations, the therapy device 110 can provide positive-pressure therapy and negative-pressure therapy to the dressing 116 at the same time (e.g., partially concurrently).

In some implementations, therapy device 110 includes a canister to receive fluid from tissue site 120 or to provide fluid to tissue site 120. In some implementations, the canister is internal to and/or integrated with therapy device 110. In other implementations, the canister is external to therapy device 110.

Therapy device 110 may also include one or more other components, such as a sensor, a processing unit/controller (e.g., a processor), an alarm indicator, a memory, a database, software, a display device, a user interface, a regulator, and/or another component, that further facilitate positive-pressure therapy or negative-pressure therapy. Additionally, or alternatively, therapy device 110 may be configured to receive fluid, exudate, and or the like via dressing 116 and tube 114. Therapy device 110 may include one or more connectors, such as a representative connector 138. Connector 130 is configured to be coupled to tube 114. Additionally, or alternatively, therapy device 110 may include one or more sensors, such a pressure sensor (e.g., a pressure transducer). The one or more sensors may be configured to enable therapy device 110 to monitor and/or sense a pressure associated with tube 114 and/or dressing 116. An illustrative example of therapy device 110 is described further herein at least with reference to FIG. 2A.

Tube 114 includes one or more lumens (e.g., one or more through conduits), such as a single lumen conduit or multiple single-lumen conduits. Tube 114 (e.g., a least one of the one or more lumens) is configured to enable fluid communication between therapy device 110 and dressing 116. For example, fluid(s) and/or exudate can be communicated between therapy device 110 and dressing 116, and/or one or more pressure differentials (e.g., positive-pressure, negative pressure, or both) can be applied by therapy device 110 to dressing 116. As an illustrative, non-limiting illustration, tube 114 is configured to deliver at least pressurized oxygen from therapy device 110 to dressing 116 to establish positive-pressure. Communication of fluid(s) and application of a pressure differential can occur separately and/or concurrently.

In some implementations, tube 114 may include multiple lumens, such as a primary lumen (e.g., a negative-pressure/fluid lumen) for application of negative-pressure and/or communication of fluid, and one or more secondary lumens proximate to or around the primary lumen. The one or more secondary lumens (e.g., one or more ancillary/peripheral lumens) may be coupled to one or more sensors (of therapy device 110), coupled to one or more valves, as an illustrative, non-limiting example. Although tube 114 is described as a single tube, in other implementations, system 100 may include multiple tubes, such as multiple distinct tubes coupled to therapy device 110, dressing 116, or both.

As used herein, a "tube" broadly refers to a tube, pipe, hose, conduit, or other structure with one or more lumens adapted to convey fluid, exudate, and/or the like, between two ends. In some implementations, a tube may be an elongated, cylindrical structure with some flexibility; however, a tube is not limited to such a structure. Accordingly, tube may be understood to include multiple geometries and rigidity. Tube 114 includes one or more lumens (e.g., one or more through conduits), such as a single lumen conduit or multiple single-lumen conduits. Tube 114 (e.g., a least one of the one or more lumens) is configured to enable fluid communication between therapy device 110 and dressing 116. For example, fluid(s) and/or exudate can be communicated between therapy device 110 and dressing 116, and/or one or more pressure differentials (e.g., positive-pressure, negative pressure, or both) can be applied by therapy device 110 to dressing 116. As an illustrative, non-limiting illustration, tube 114 is configured to deliver at least pressurized oxygen from therapy device 110 to dressing 116 to establish negative-pressure. Communication of fluid(s) and application of a pressure differential can occur separately and/or concurrently.

Referring to FIG. 1B, an illustrative example of a cross-section of tube 114 (in which tube 114 comprises a single lumen) along line A-A of FIG. 1A is shown. Tube 114 may include a primary lumen 121 (e.g., a negative-pressure/fluid lumen). In other implementations, tube 114 may include one or more secondary lumens, such as a positive-pressure/fluid lumen, one or more sense lumens, etc., or a combination thereof, such as described with reference to at least FIG. 2B. Although tube 114 has been described and/or shown as having a circular cross-sectional shape, in other implementations, tube 114 may have a cross-sectional shape other than a circle, such as an oval, triangle, quadrilateral, pentagon, star, or another shape, as illustrative, non-limiting examples.

Referring to FIG. 1A, dressing 116 includes a connector 130 (also referred to as a dressing connection pad or a pad), a drape 132, and a manifold 134 (also referred to as a distribution manifold or an insert). Drape 132 may be coupled to connector 130. To illustrate, drape 132 may be coupled to connector 130 via an adhesive, a separate adhesive drape over at least a portion of connector 130 and at least a portion of drape 132, or a combination thereof, as illustrative, non-limiting examples. In some implementations, dressing 116 may include one or more pressure sensors 152 configured to determine a pressure at the wound site and to provide pressure data to a controller of therapy device 110. In other implementations, a pressure sensor or sensors may be included in the therapy device 110, as further described with reference to FIG. 2. The pressure sensors in the therapy device 110 may determine a pressure of the pressure source (e.g., pump 150) or a pressure of the wound site, such as via tube 114.

Drape 132 may be configured to couple dressing 116 at tissue site 120 and/or to provide a seal to create an enclosed space (e.g., an interior volume) corresponding to tissue site 120. For example, drape 132 may be configured to provide a fluid seal between two components and/or two environments, such as between a sealed therapeutic environment and a local ambient environment. To illustrate, when coupled to tissue site 120, drape 132 is configured to maintain a pressure differential (provided by a positive-pressure source or a negative-pressure source) at tissue site 120. Drape 132 may include a drape aperture that extends through drape 132 to enable fluid communication between device and target tissue. Drape 132 may be configured to be coupled to tissue site 120 via an adhesive, such as a medically acceptable, pressure-sensitive adhesive that extends about a periphery, a portion, or an entirety of drape 132. Additionally, or alternatively, drape 132 may be coupled to tissue site 120 via a double-sided drape tape, paste, hydrocolloid, hydrogel, and/or other sealing device or element, as illustrative, non-limiting examples.

Drape 132 may include an impermeable or semi-permeable, elastomeric material, as an illustrative, non-limiting example. In some implementations, drape 132 may be liquid/gas (e.g., moisture/vapor) impermeable or semi-permeable. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane (PU), EVA film, co-polyester, and silicones. In some implementations, drape 132 may include the "V.A.C.® Drape" commercially available from KCI. Additional, specific non-limiting examples of materials of drape 132 may include a silicone drape, 3M Tegaderm® drape, and a polyurethane (PU) drape such as one available from Avery Dennison Corporation of Pasadena, Calif. An additional, specific non-limiting example of a material of the drape 132 may include a 30 micrometers (μm) matt polyurethane film such as the Inspire™ 2317 manufactured by Exopack™ Advanced Coatings of Matthews, N.C.

Manifold 134 is configured to be positioned on and/or near tissue site 120, and may be secured at the tissue site 120, such as secured by drape 132. The term "manifold" as used herein generally refers to a substance or structure that may be provided to assist in applying a pressure differential (e.g., negative-pressure differential) to, delivering fluids to, or removing fluids and/or exudate from a tissue site and/or target tissue. The manifold typically includes a plurality of flow channels or pathways that distribute fluids provided to and removed from the tissue site. In an illustrative implementation, the flow channels or pathways are interconnected to improve distribution of fluids provided to or removed from the tissue site. Manifold 134 may be a biocompatible material that may be capable of being placed in contact with the tissue site and distributing positive and/or negative-pressure to the tissue site. Manifold 134 may include, without limitation, devices that have structural elements arranged to form flow channels, such as foam, cellular foam, open-cell foam, porous tissue collections, liquids, gels, and/or a foam that includes, or cures to include, flow channels, as illustrative, non-limiting examples. Additionally, or alternatively, manifold may include polyethylene, a polyolefin, a polyether, polyurethane, a co-polyester, a copolymer thereof, a combination thereof, or a blend thereof.

In some implementations, manifold 134 is porous and may be made from foam, gauze, felted mat, or other material suited to a particular biological application. In a particular implementation, manifold 134 may be a porous foam and may include a plurality of interconnected cells or pores that act as flow channels. The foam (e.g., foam material) may be either hydrophobic or hydrophilic. As an illustrative, non-limiting example, the porous foam may be a polyurethane, open-cell, reticulated foam such as GranuFoam® material manufactured by Kinetic Concepts, Incorporated of San Antonio, Tex.

In some implementations, manifold 134 is also used to distribute fluids such as medications, antibacterials, growth factors, and other solutions to the tissue site. Other layers may be included in or on manifold 134, such as absorptive materials, wicking materials, hydrophobic materials, and hydrophilic materials. In an implementation in which the manifold 134 includes a hydrophilic material, manifold 134 may be configured to wick fluid away from tissue site 120 and to distribute negative pressure and/or positive-pressure to tissue site 120. The wicking properties of manifold 134 may draw fluid away from the tissue site 120 by capillary flow or other wicking mechanisms. An illustrative, non-limiting example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether and/or foams that have been treated or coated to provide hydrophilicity.

In some implementations, manifold 134 is constructed from bioresorbable materials that do not have to be removed from tissue site 120 following use of the system 100. Suitable bioresorbable materials may include, without limitation, a polymeric blend of polylactic acid (PLA) and polyglycolic acid (PGA). The polymeric blend may also include without limitation polycarbonates, polyfumarates, and capralactones. Manifold 134 may further serve as a scaffold for new cell-growth, or a scaffold material may be used in conjunction with manifold 134 to promote cell-growth. A scaffold may be a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials. Although a manifold 134 is illustrated in FIG. 1A, in other implementations, dressing 116 does not include manifold 134. In such implementations, drape 132 of dressing 116 is coupled to connector 130.

Connector 130 includes a body 142 (e.g., a housing) and a base 144, and is configured to be coupled to tube 114 via an interface 146 (e.g., a port). Base 144 is configured to be coupled to dressing 116. For example, base 144 may be coupled, such as via an adhesive, to drape 132 and/or manifold 134. In some implementations, base 144 comprises a flange that is coupled to an end of body 142 and/or is integrally formed with body 142. Connector 130, such as body 142, base 144, interface 146, or a combination thereof, may be made of rigid material and/or a semi-rigid material. In a non-limiting example, connector 130 may be made from a plasticized polyvinyl chloride (PVC), polyurethane, cyclic olefin copolymer elastomer, thermoplastic elastomer, poly acrylic, silicone polymer, or polyether block amide copolymer. In some implementations, connector 130 is formed of a semi-rigid material that is configured to expand when under a force, such as positive-pressure greater than or equal to a particular amount of pressure. Additionally or alternatively, connector 130 may be formed of a semi-rigid material that is configured to collapse when under a force, such as reduced-pressure less than or equal to a threshold pressure.

Body 142 includes one or more channels or one or more conduits that extend from and/or are coupled to interface 146. To illustrate, body 142 may include a primary channel configured to be coupled in fluid communication with a primary lumen (e.g., 121) of tube 114. The primary channel may be coupled to a cavity (e.g., a tissue cavity partially defined by body 142) having an aperture open towards manifold 134 (and/or towards tissue site 120). For example, the primary channel may include a first opening associated with interface 146 and a second opening (distinct from the aperture of the cavity) associated with the cavity. Thus, the primary channel may define a through channel of body 142 to enable fluid communication between interface 146 and tissue site 120.

Body 142 includes a channel (e.g., a through channel) having a first aperture open opposite dressing 116 and a second aperture open towards dressing 116. For example, the first aperture is located on an outer surface side (e.g., an ambient environment surface) of connector 130 and the second aperture is located on an inner surface side (e.g., a tissue facing side) of connector 130. The second aperture is configured to be coupled to one or more lumens of tube 114, such as coupled via the cavity. Illustrative, non-limiting examples of commercially available connectors include a "V.A.C. T.R.A.C.® Pad," or "Sensa T.R.A.C.® Pad" available from Kinetic Concepts, Inc. (KCI) of San Antonio, Tex.

During operation of system 100, dressing 116 is coupled to tissue site 120 over a wound. Additionally, dressing 116 is coupled to therapy device 110 via tube 114. Negative-pressure or positive-pressure can be applied to dressing 116 (e.g., an interior volume of dressing 116) by a pump 150 (e.g., a pressure source) associated with therapy device 110. In some implementations, pump 150 is a silent or inaudible to a human. In a particular implementation, pump 150 is a piezoelectric pump that is substantially inaudible to a human ear. For example, pump 150 may be configured to operate at frequencies above substantially 10 kilohertz, which are silent (or substantially inaudible) to the human ear. Pump 150 may be configured to be worn by a user. For example, pump 150 (or therapy device 110) may be light enough to be attached to a person with adhesive, an attachment means, such as hook, clip, loop, etc., or both. Additionally, pump 150 (or therapy device 110) may be configured to maintain a temperature that is low enough to avoid causing burns to the user. Additionally, pump 150 (or therapy device 110) may be small enough to be discreetly worn underneath clothing. In some implementations, therapy device 110 is a single use, disposable device.

A controller of therapy device 110 may operate pump 150 in multiple operating modes (i.e., two or more operating modes). In some implementations, the controller of therapy device 110 may operate pump 150 in one of at least three operating modes including a first operating mode (e.g., a "boost operating mode"), a second operating mode (e.g., a "normal power operating mode"), and a third operating mode (e.g., a "reduced power operating mode"). Selection of which operating mode to operate pump 150 may be based on a variety of conditions, such as power-on conditions, leak conditions, and low battery conditions.

To illustrate, the controller may transition pump 150 into the boost operating mode responsive to detecting a power-on of therapy device 110. The boost operating mode is associated with a first drive voltage that is greater than a second drive voltage associated with the normal power operating mode and the reduced power operating mode. Thus, the boost operating mode may drain the batteries of the therapy device 110 faster than the other operating modes. To compensate, the boost operating mode may be used only until a target pressure is output by pump 150. By providing a higher drive voltage to pump 150 during the boost operating mode, pump 150 may more quickly reach the target pressure, and thus the boost operating mode decreases an amount of time between power-on of the therapy device 110 and a when a therapeutic amount of pressure is output by pump 150. Additionally, or alternatively, the controller may increase a duty cycle of pump 150 during operation in the boost operating mode, which may cause pump 150 to more quickly reach the target pressure. Once the target pressure is reached, the controller may transition pump 150 into the normal power operating mode.

While operating in the normal power operating mode, pump 150 may provide a therapeutic amount of pressure within a first pressure range. For example, a duty cycle of pump 150 may be set within a first duty cycle range that enables output of pressure in the first pressure range. In a particular implementation, the first pressure range is from 100 mm Hg to 150 mm Hg, with a first target pressure of 125 mm Hg. In other implementations, other pressure ranges may be used, such as 115 mm Hg to 135 mm Hg, as a non-limiting example. Operation of pump 150 in the normal power operating mode may continue as long as normal conditions continue (e.g., no leak condition or low battery condition is detected).

If a leak condition or a low battery condition is detected, the controller may transition pump 150 to the reduced power operating mode. The reduced power operating mode is associated with a second duty cycle range that is different from the first duty cycle range associated with the normal power operating mode. For example, the second duty cycle range may be less than the first duty cycle range (e.g., at least some values in the second duty cycle range may be less than the values in the first duty cycle range). Setting the duty cycle of pump 150 in the second duty cycle range may enable output of a pressure within a second pressure range (e.g., a therapeutic pressure that is less than the pressure output in the normal power operating mode). In a particular implementation, the second pressure range is from 50 mm Hg to 100 mm Hg with a target pressure of 75 mm Hg. In other implementations, other pressure ranges may be used, such as 65 mm Hg to 85 mm Hg, as a non-limiting example. Because the second duty cycle range is less than the first duty cycle range, an average power used during the reduced power operating mode is less than an average power used during the normal power operating mode. Thus, operation of pump 150 in the reduced power operating mode may extend a duration of time that therapeutic pressure is output by the pump by reducing the amount of battery power used to operate.

Thus, system 100 enables operation of pump 150 in multiple different operating modes. The multiple operating modes provide benefits as compared to conventional pumps that operate in a single operating mode. For example, operating in the boost operating mode enables pump 150 to more quickly output a therapeutic amount of pressure. As another example, operating in the reduced power operating mode provides a lesser amount, but still a therapeutic amount, of pressure from pump 150 while conserving power and extending the battery life of therapy device 110. Extending the battery life of therapy device 110 enables a user to use therapy device 110 for longer periods of time between recharges, even when leaks occur, such that the user can perform activities away from home (or other charging location) without having to worry about therapy device 110 ceasing to function, which improves user trust in therapy device 110.

Additionally, such power saving efficiency can be utilized to employ silent or inaudible pumps. As inaudible pumps are less energy efficient, the increased power saving from employing multiple operating modes enables a battery to power a silent pump for 12-18 hours. As illustrative examples, diaphragm based pumps for disposable, discreet therapy systems have 10-30 percent energy efficiency. A piezoelectric pump for a disposable, discreet therapy system may have an energy efficiency of about 2 percent.

Referring to FIG. 2A, an illustrative example of an illustrative system 200 (e.g., a negative-pressure therapy system) is shown. System 200 includes a negative-pressure therapy device 210 (e.g., a positive-pressure therapy apparatus), a tube 214, and a dressing 216. System 200 may optionally include a mobile device 218. Dressing 216 is coupled to device 210 via tube 214. Device 210 and dressing 216 may include or correspond to therapy device 110 and dressing 116, respectively. Tube 214 may include or correspond to tube 114.

Referring to FIG. 2B, an illustrative example of a cross-section of tube 214 (when tube 114 comprises multiple lumens) along line B-B of FIG. 2A is shown. Tube 214 may include a primary lumen 221 (e.g., a negative-pressure/fluid lumen) and one or more secondary lumens, such as a first secondary lumen 222 (e.g., a positive-pressure/fluid lumen), a second secondary lumen 224 (e.g., a first sense lumen), a third secondary lumen 226 (e.g., a second sense lumen), and a fourth secondary lumen 228 (e.g., a third sense lumen). Although described as having a single primary lumen (e.g., 221), tube 214 may have multiple primary lumens, such as a first primary lumen for negative-pressure and a second primary lumen for positive-pressure. Additionally, or alternatively, primary lumen 221 may be configured to for both positive-pressure and negative-pressure. Although described as having four secondary lumens, in other implementations, tube 214 may include fewer than or more than four secondary lumens. Although tube 214 has been described and/or shown as having a circular cross-sectional shape, in other implementations, tube 214 may have a cross-sectional shape other than a circle, such as an oval, triangle, quadrilateral, pentagon, star, or another shape, as illustrative, non-limiting examples. In an alternative implementation, primary lumen 221 may be a positive-pressure/fluid lumen, first secondary lumen 222 may be a negative-pressure/fluid lumen), a secondary lumens 224, 226, 228 may be sense lumens.

Dressing 216 is configured to be coupled to (e.g., adhered to) a tissue site 220 of a patient. Tissue site 220 may include or correspond to tissue site 120. Dressing 216 may include one or more components, such as a connector 230, a drape 232, a manifold 234, or a combination thereof, as illustrative, non-limiting examples. Connector 230 may include or correspond to connector 130. Drape 232 and manifold 234 may include or correspond to drape 132 and manifold 134, respectively. Drape 232 may be coupled to connector 230 and/or manifold 234, and may include an opening 235 (e.g., a drape aperture) to enable communication (e.g., fluid communication) between connector 230 and manifold 234.

As shown, drape 232 is coupled to tissue site 220 via a representative adhesive 237, such as a medically acceptable, pressure-sensitive adhesive that extends about a periphery, a portion, or an entirety of drape 232. Additionally, or alternatively, drape 232 may be coupled to tissue site 220 via a double-sided drape tape, paste, hydrocolloid, hydrogel, and/or other sealing device or element, as illustrative, non-limiting examples. Drape 232 is configured to be coupled to tissue site 220 such that drape 232 covers manifold 234 (and target tissue 236) to form and/or define an interior volume 238 between drape 232 and tissue site 220 (e.g., target tissue 236). To illustrate, interior volume 238 may correspond to a sealed therapeutic environment. For example, the tissue proximate the target tissue 236 may be undamaged epidermis peripheral to target tissue 236. The sealed therapeutic environment may be isolated from an external environment, such as an external environment at ambient pressure.

As shown, manifold 234 is positioned within interior volume 238 at (e.g., on or above) target tissue 236 of tissue site 220. In some implementations, manifold 234 may contact tissue site 220, target tissue 236, or both. In some implementations, such as when target tissue 236 extends into tissue from a tissue surface 219 creating a cavity, manifold 234 may partially or completely fill the cavity. In other implementations, manifold 234 may be placed over target tissue 236. Manifold 234 may take one or more forms, and/or may have one or more configurations (e.g., sizes, shapes, and/or thicknesses), depending on one or more factors, such as the type of treatment being implemented, the nature and size of target tissue 236, a stage of treatment, or a combination thereof. For example, the size and shape of the manifold 234 may be adapted to target tissue 236 and/or tissue site 220. To illustrate, manifold 234 may be adapted to contours of target tissue 236 and/or tissue site 220. In a particular implementation, manifold 234 includes a foam, such as GranuFoam® material manufactured by Kinetic Concepts, Incorporated of San Antonio, Tex., as an illustrative, non-limiting example.

Connector 230 may include a connector body 242, a base 244, and an interface 246 (e.g., a port). Connector body 242 (e.g., a housing) may include or correspond to body 142. Base 244 may include or correspond to base 144. Interface 246 may include or correspond to interface 146. Interface 246 is configured to be coupled to tube 214.

Further, connector body 242 may include one or more channels or conduits that extend from and/or are coupled to interface 246. For example, connector body 242 may include a conduit and a secondary channel (e.g., a reduced-pressure or exudate channel) that are in fluid communication with interior volume 238. To illustrate, the secondary channel may have an aperture defined by base 244, and which is positioned over manifold 234, to enable fluids and/or exudate to be drawn from target tissue 236. In some implementations, connector 230 may be positioned on manifold 234 such that a perimeter of the aperture (defined by base 244) is in direct contact with manifold 234. When the conduit and the second channel are in fluid communication with interior volume 238, connector 230 may operate to maintain fluid communication between interior volume 238 and device 210 via tube 214, and to prevent fluid communication between interior volume (e.g., a sealed therapeutic environment formed by dressing 216) and the ambient environment.

Tube 214 includes one or more lumens. For example, tube 214 may include a negative-pressure/fluid lumen (e.g., 221), a positive-pressure/fluid lumen, and one or more sense lumens. As shown, a first end of tube 214 is coupled to dressing 216 and a second end of tube 214 is coupled to device 210. In some implementations, the second end of tube 214 may include a therapy device connector configured to couple (e.g., mate) with device 210.

Device 210 includes a controller 260, one or more interfaces 262, one or more I/O devices 264, and one or more connectors, such as a representative connector 266. Device 210 further includes one or more conduits 268, a fluid chamber 270, pressure sensors 272, 274, one or more valves 276 (e.g., solenoid valves), and a reduced-pressure source 278.

Connector 266, such as connector 138, is configured to be coupled to tube 214, such as the second end of tube 214. Connector 266 includes one or more ports/interfaces, such as a first port/interface 280, a second port/interface 282, a third port/interface 284, a fourth port/interface 286. When connector 266 is coupled to tube 214, the positive-pressure/fluid lumen (e.g., 221) is in fluid communication with first port/interface 280, the negative-pressure/fluid lumen (e.g., 222) is in fluid communication with second port/interface 282, first sense lumen (e.g., 224) is in fluid communication with third port/interface 284, and second sense lumen (e.g., 226) is in fluid communication with fourth port/interface 286.

Each of first port/interface 280, second port/interface 282, third port/interface 284, and fourth port/interface 286 is coupled to one or more components of device 210 via one or more conduits (e.g., 268). For example, first port/interface 280 is coupled to reduced-pressure source 278, second port/interface 282 is coupled through fluid chamber 270 (e.g., a canister or a liquid-collection cavity) to positive-pressure source 279, third port/interface 284 is coupled to a first pressure sensor 272, and fourth port/interface 286 is coupled to a second pressure sensor 274. The pressure sensors 272, 274 may be configured to generate data indicative of pressure within dressing 216. Although described as having two pressure sensors (e.g., 272, 274), in other implementations, device 210 may include fewer than two pressure sensors, such as no pressure sensors or a single pressure sensor, or more than two pressure sensors. Additionally, each of first port/interface 280, second port/interface 282, third port/interface 284, and fourth port/interface 286 is coupled to a corresponding valve (e.g., 276), such as a solenoid valve, which is configured to change pressure from dressing 216. First port/interface 280 is coupled to reduced-pressure source 278 and a corresponding valve 276 via a conduit 268.

Reduced-pressure source 278 is configured to provide reduced or negative-pressure to interior volume 238 of dressing 216 such that interior volume 238 is reduced, and/or negative-pressure is applied to at least target tissue 236. Reduced-pressure source 278 may include a mechanically and/or electrically-powered device, such as a manually-actuated or manually-charged pump (e.g., 150), a vacuum pump, an electrically-driven vacuum pump, a suction pump, a wall suction port, a micro-pump, a disc-pump, and/or the like, as illustrative, non-limiting examples. As illustrated in FIG. 2A, the reduced-pressure source 278 and the positive-pressure source 279 may operate in conjunction with each other and are applied to different portions of tissue site 220 via different lumens (e.g., 221, 222) of tube 214. In other implementations, the reduced-pressure source 278 and the positive-pressure source 279 share a lumen (e.g., 221 or 222) of tube 214 and the positive-pressure source 279 operates in the alternative to the reduced-pressure source 278 (e.g., operate in distinct cycles). For example, the positive-pressure source 279 operates before or after the reduced-pressure source 278 to remove exudate from tissue site 220. In some implementations, reduced-pressure source 278 includes a piezoelectric pump that is substantially silent to the human ear. In an alternate implementation, reduced-pressure source 278 is replaced with a positive-pressure source (e.g., pump 150) configured to apply positive pressure to target tissue 236.

In some implementations, device 210 further includes positive-pressure source 279 that is configured to provide positive-pressure to interior volume 238 of dressing 216 such that interior volume 238 is expanded, and/or positive-pressure is applied to at least target tissue 236. Positive-pressure source 279 may include a mechanically and/or electrically-powered device, such as a manually-actuated or manually-charged pump (e.g., 150), an oxygen tank, an oxygen collector, a wall port, a micro-pump, a disc-pump, and/or the like, as illustrative, non-limiting examples.

Controller 260 includes a processor 290 coupled to a memory 293 (e.g., a computer-readable storage device). Memory 293, such as a non-transitory computer-readable storage medium, may include volatile memory devices (e.g., random access memory (RAM) devices), nonvolatile memory devices (e.g., read-only memory (ROM) devices, programmable read-only memory, and flash memory), or both. Memory 293 may be configured to store instructions 294, a pressure profile 296, and one or more thresholds 295. Instructions 294 may be configured to, when executed by the one or more processors 290, cause the processor(s) 290 to perform one or more operations.

Pressure profile 296 may include desired target pressures to be provided to a patient over a time period. In some implementations, the pressure profile 296 may include a set-up profile applying target pressures at the commencement of therapy treatments and a maintenance profile for applying target pressure during therapy. One or more thresholds 295 may include one or more one or more pressure thresholds, one or more time thresholds, one or more leak counter thresholds, one or more seal counter thresholds, one or more other thresholds, or a combination thereof.

Processor 290 may include a microcontroller/microprocessor, a central processing unit (CPU), a field-programmable gate array (FPGA) device, an application-specific integrated circuits (ASIC), another hardware device, a firmware device, or any combination thereof. Processor 290 may be configured to execute instructions 294, execute and/or operate according to pressure profile 296, and/process sensor data generate by pressure sensors 272, 274. For example, processor 290 may be configured to process sensor data (e.g., pressure signals) received by one or more sensors (e.g., 272, 274) and/or monitor the sensor data. Additionally, or alternatively, processor 290 may be configured to issue one or more alerts according to a pre-determined pressure therapy (e.g., pressure profile 296) for a patient and/or based on one or more thresholds 295. In some implementations, the one or more alerts may be in the form of a visual alert (e.g., a light indicator), a tactile alert, an audible alert, a message presented via a display, or a message transmitted to another device. In the event that processor 290 determines that pressure profile 296 is being implemented, processor 290 may provide an indication that the sensor data (e.g., the monitored pressure at dressing 216) is following pressure profile 296. For example, processor 290 may initiate a visual indication (e.g., a light indicator), a tactile indication, an audible indication, a message presented via a display, or a message transmitted to another device.

The one or more interfaces 262 may include a wired interface, a wireless interface, or both. In some implementation, the one or more interfaces 262 may include a network interface and/or a device interface configured to be communicatively coupled to one or more other devices. For example, interfaces 262 may include a transmitter, a receiver, or a combination thereof (e.g., a transceiver), and may enable wired communication, wireless communication, or a combination thereof. Additionally, or alternatively, the one or more interfaces 262 may include serial interfaces (e.g., universal serial bus (USB) interfaces or Institute of Electrical and Electronics Engineers (IEEE) 1394 interfaces), parallel interfaces, display adapters, audio adapters, and other interfaces. The one or more I/O devices 264 may include a mouse, a keyboard, pointing devices, a display device, the camera, speakers, microphones, touch screens, other I/O devices, or a combination thereof. Processor 290 may configured to send and/or receive data via the interface(s) 262 and/or the I/O device(s) 264.

During operation, dressing 216 is coupled to tissue site 220 so as to cover target tissue 236. Additionally, dressing 216 is coupled to device 210 via tube 214. In some implementations, processor 290 receives an input via I/O device(s) 264, such as a touchscreen, to select a pressure profile (e.g., 296) of multiple pressure profiles stored at memory 293, to initiate positive-pressure therapy, or both. Alternatively, the input may indicate a value of a positive-pressure to be provided and/or maintained. Responsive to the input, controller 260 (e.g., processor 290) generates one or more commands to initiate operations of one or more components of device 210. For example, processor 290 may access pressure profile 296 (e.g., a set-up profile or a maintenance profile). Additionally, or alternatively, processor 290 may activate and/or regulate reduced-pressure source 278, one or more valves 276, or both. In some implementations, processor 290 may control operation of reduced-pressure source 278, one or more valves 276 based on at least in part on the input (e.g., the pressure profile 296 selection or the value of the reduced or negative-pressure).

Responsive to one or more signals (e.g., commands) from processor 290, reduced-pressure source 278 may apply negative-pressure to dressing 216. For example, negative-pressure developed by reduced-pressure source 278 may be delivered through tube 214 to connector 230 of dressing 216. Accordingly, the reduced-pressure source 278 can decrease a pressure in interior volume 238. Internal volume (e.g., a sealed therapeutic environment) and/or target tissue 236 may be isolated from an external environment (associated with an ambient pressure).

As negative-pressure is provided via pressure/fluid lumen (e.g., 221), pressure at dressing 216 may be communicated to first pressure sensor 272 and second pressure sensor 274 via first sense lumen (e.g., 224) and second sense lumen (e.g., 226), respectively. The pressure communicated by via first sense lumen (e.g., 224) and second sense lumen (e.g., 226) may be representative of the pressure at the target tissue 236. Each of first pressure sensor 272 and second pressure sensor 274 are configured to generate sensor data that is communicated to controller 260 (e.g., processor 290). The sensor data provided to controller 260 enables device 210 to track treatment provided to target tissue 236 via dressing 216. Based on the sensor data, controller 260 (e.g., processor 290) may initiate operation of one or more valves (e.g., 276) between an open position and a closed position. For example, processor 290 may be configured to adjust a particular valve in response to a comparison of the sensor data (indicating that a pressure within the interior volume (e.g., 238) to a threshold (e.g., 295).

In some implementations, processor 290 is configured to control reduced-pressure source 278 (e.g., a reduced-pressure source device) and/or one or more valves 276 based at least in part on the sensor data. For example, processor 290 may be configured to deactivate reduced-pressure source 278 in response to a determination that the sensor data indicates that a pressure within the interior volume (e.g., 238) is less than a first threshold (e.g., a first threshold pressure value). In some implementations, processor 290 is configured to operate at least one valve (e.g., 276) towards the open position upon or after deactivation of reduced-pressure source 278. To illustrate, the at least one valve may include the valve coupled to reduced-pressure source 278, the valve coupled to first pressure sensor 272, and/or the valve coupled to second pressure sensor 274. As another example, processor 290 may be configured to activate reduced-pressure source 278 in response to a determination that the sensor data indicates that a pressure within the interior volume (e.g., 238) is greater than or equal to a second threshold (e.g., a second threshold pressure value). Activation of reduced-pressure source 278 may decrease pressure within the interior volume (e.g., 238). In some implementations, processor 290 is configured to operate at least one valve (e.g., 276) towards the closed position upon or after activation of reduced-pressure source 278. The first threshold and the second threshold may have the same value. Alternatively, the first threshold and the second threshold may have different values (e.g., the second threshold may be greater than the first threshold).

In some implementations, valve 276 coupled to first pressure sensor 272 may be operated independent of valve 276 coupled to second pressure sensor 274. For example, controller 260 may operate valve 276 coupled to first pressure sensor 272 based on sensor data received from first pressure sensor 272 and/or based on a first set of one or more thresholds (e.g., 295). Controller 260 may operate valve 276 coupled to second pressure sensor 274 based on sensor data received from second pressure sensor 274 and/or based on a second set of one or more thresholds (e.g., 295). The first set of one or more thresholds and the second set of one or more thresholds may include one or more of the same threshold value(s) and/or one or more different threshold value(s). Additionally, or alternatively, in other implementations, controller 260 may operate one or more of the valves based on an average of sensor data of two or more sensors. For example, controller 260 may control one or more valves, such as the valve coupled to reduced-pressure source 278 based on an average of the sensor data (received from pressure sensors 272, 274) and a third set of one or more thresholds. The third set of one or more thresholds may include one or more of the same threshold value(s) and/or one or more different threshold value(s) as the first set of one or more thresholds and/or the second set of one or more thresholds.

Reduced-pressure provided by reduced-pressure source 278 via tube 214 can cause exudate, fluid, and/or another material to be drawn (e.g., removed) from target tissue 236 (e.g., tissue site 220) via tube 214 (e.g., reduced-pressure/fluid lumen) and second port/interface 282. Exudate, fluid, and/or another material removed via first port/interface 280 may be collected in fluid chamber 270 (e.g., a canister) for disposal. In some implementations, device 210 may include a sensor (not shown) coupled to controller 260 (e.g. processor 290) and configured to monitor a volume of fluid chamber 270. For example, processor 290 may receive sensor data from the sensor that indicates a fill level of fluid chamber 270. In response to a determination by processor 290 that the fill level is greater than or equal to a threshold (e.g., a threshold fill level value), processor 290 is configured to deactivate reduced-pressure source 278, operate at least one valve (e.g., 276) towards the open position, or both. Additionally, or alternatively, based on a determination by processor 290 that the fill level is greater than or equal to a threshold, processor 290 may initiate a notification (e.g., an alarm), such as a message via a display, an audio and/or visual notification, transmit a data message to another device, or a combination thereof.

Positive-pressure provided by positive-pressure source 279 via tube 214 can cause pressurized fluid (e.g., oxygen) to be provided to target tissue 236 (e.g., tissue site 220) via tube 214 (e.g., positive-pressure/fluid lumen) and second port/interface 282. In some implementations, device 210 may include a sensor and/or regulator (not shown) coupled to controller 260 (e.g. processor 290) and configured to monitor a pressure of the positive-pressure source 279 or the corresponding conduit 268 thereof. For example, processor 290 may receive sensor data from the sensor that indicates a pressure level of the regulator and may operate valve 276 to control a pressure and/or volume of positive-pressure source 279. Once a desired pressure of fluid is achieved, the pressurized fluid (e.g., oxygen) may be provided to target tissue 236.

In some implementations, controller 260 (e.g., processor 290) is configured to operate a pump (e.g., pump 150, reduced-pressure source 278, positive-pressure source 279, or a combination thereof) in multiple operating modes. As illustrated in FIG. 2A controller 260 (e.g., processor 290) the configured to operate reduced-pressure source 278 in one of at least three different operating modes. The at least three operating modes include a first operating mode 297 (a "boost operating mode"), a second operating mode 298 (a "normal power operating mode"), and a third operating mode 299 (a "reduced power operating mode"). The different operating modes may be associated with different drive voltages of the pump and/or different duty cycle ranges of the pump. In other implementations, the controller 260 (e.g., processor 290) is configured to operate reduced-pressure source 278 in two operating modes or four or more operating modes. As illustrative examples, the two operating modes may include the boost operating mode and the normal power operating mode or the normal power operating mode and the reduced power operating mode. As an additional example, the four or more operating modes may include the boost operating mode, the normal power operating mode, a first reduced power mode (e.g., leak detected mode), and a second reduced power mode (e.g., low battery mode). Additionally or alternatively, the controller 260 (e.g., processor 290) is configured to operate reduced-pressure source 278 in two boost operating modes, such as a first boost operating mode for startup and a second boost operating mode for when a leak is detected and one or more other conditions are satisfied (e.g., above a threshold, such as 75 percent or responsive to user input).

Controller 260 may operate the pump (e.g., pump 150, reduced-pressure source 278, positive-pressure source 279, or a combination thereof) in the first operating mode 297 responsive to detecting a power-on event. For example, when device 210 is powered on, controller 260 may operate the pump in the first operating mode 297 to cause the pump to more quickly reach output of a therapeutic amount of pressure (as compared to operating in the second operating mode 298). The first operating mode 297 is associated with a first drive voltage that is greater than a second drive voltage associated with the second operating mode 298 (and the third operating mode 299). Thus, by providing more drive voltage to the pump, the controller 260 may cause the pump to more quickly reach output of a therapeutic amount of pressure. In a particular implementation, a target amount of pressure to be reached by operation in the first operating mode is 75 mm Hg. In other implementations, the target pressure may be greater than or less than 75 mm Hg, such as 50 mm Hg, 100 mm Hg, or 125 mm Hg, as non-limiting examples. After reaching the target pressure, as indicated by pressure data from pressure sensors 272, 274, controller 260 transitions the pump from first operating mode 297 to second operating mode 298, as further described with reference to FIG. 6.

While operating the pump in second operating mode 298, controller 260 changes (e.g., reduces) the drive voltage to the pump (as compared to operation in first operating mode 297). Additionally, controller 260 may adjust a duty cycle of the pump to cause output of a second target pressure. The second target pressure may correspond to an amount of pressure to be applied during normal operating conditions. In a particular implementation, the second target pressure is 125 mm Hg. In other implementations, the second target pressure may be greater than or less than 125 mm Hg, such as 100 mm Hg, 115 mm Hg, 135 mm Hg, or 150 mm Hg, as non-limiting examples.

Controller 260 (e.g., processor 290) may also maintain a leak counter 291 to detect if a leak occurs, such as a leak at the dressing 216. For example, during operation in second operating mode 298, if the measured pressure is substantially less than the second target pressure for more than a threshold period of time, controller 260 may increment leak counter 291. In a particular implementation, the threshold period of time is 60 seconds. In other implementations, the threshold period of time is greater than or less than 60 seconds, such as 30 seconds, 45 seconds, 75 seconds, 90 seconds, or 120 seconds, as non-limiting examples. Controller 260 may compare leak counter 291 to a leak threshold to determine whether a leak has occurred. The leak threshold may be 1, 2, 3, 5, 7, 10, or 15, as non-limiting examples. When the leak threshold is 1, the leak counter 291 corresponds to leak indicator or flag, i.e., a count value of 1 indicates a leak condition and a count value of 0 indicates a lack of a leak or a seal condition. If leak counter 291 satisfies (e.g., is greater than or equal to) the leak threshold, a leak is detected, and controller 260 initiates an alert and transitions the pump into third operating mode 299. Additionally, or alternatively, if a battery level of one or more batteries of device 210 is less than or equal to a battery level threshold, controller 260 initiates an alert and transitions the pump into third operating mode 299, as further described with reference to FIG. 7.

While operating the pump in third operating mode 299, controller 260 changes (e.g., reduces) the duty cycle range associated with the pump. For example, controller 260 may reduce the duty cycle of the pump such that the pump outputs a third target pressure. In a particular implementation, the third target pressure is 75 mm Hg. In other implementations, the third target pressure may be greater than or less than 75 mm Hg, such as 50 mm Hg, 65 mm Hg, 85 mm Hg, 90 mm Hg, or 100 mm Hg, as non-limiting examples. Reducing the duty cycle of the pump may reduce the average power consumed by the pump, which preserves battery charge at device 210 for a longer amount of time than operation in the second operating mode 298.

During operation in the third operating mode 299, controller 260 may initiate transmission of a leak alert, a low battery alert, or both, to mobile device 218. Additionally, or alternatively, the pump (e.g., pump 150, reduced-pressure source 278, and/or positive-pressure source 279) or device 210 may include one or more indicators, such as lights, and a leak alert, a low power alert, or both may be initiated by controller 260 turning on one or more of the indicators (or issuing another type of notification, such as an audible notification, a haptic notification, etc.).

Controller 260 (e.g., processor 290) may also maintain a seal counter 292 to detect if a seal occurs (e.g., a leak at dressing 216 has been sealed). For example, during operation in third operating mode 299, if the measured pressure is substantially greater than or equal to the third target pressure, controller 260 may increment seal counter 292. Controller 260 may compare seal counter 292 to a seal threshold to determine whether a seal has occurred. The seal threshold may be 1, 2, 3, 5, 7, 10, or 15, as non-limiting examples. When the seal threshold is 1, the seal counter 292 corresponds to seal indicator or flag, i.e., a count value of 1 indicates a seal condition and a count value of 0 indicates a lack of seal or leak condition. If seal counter 292 satisfies (e.g., is greater than or equal to) the seal threshold, a seal is detected. If a seal is detected, the battery level is compared to the battery level threshold and, if the battery level is greater than the battery level threshold, controller 260 transitions the pump to second operating mode 298, as further described with reference to FIG. 8.

In a particular implementation, a wound therapy device (e.g., 210) includes a pump (e.g., 150, 278, and/or 279) configured to be worn by a user and a controller (e.g., 260) configured to transition the pump from operating in a first operating mode (e.g., 297) to operating in a second operating mode (e.g., 298) responsive to a pressure of the wound therapy device satisfying a first pressure threshold (e.g., 295). The first operating mode is associated with a first drive voltage that is different from a second drive voltage associated with the second operating mode.

In another particular implementation, a wound therapy device (e.g., 210) includes a pump (e.g., 150, 278, and/or 279) configured to be worn by a user and a controller (e.g., 260) configured to operate the pump in one of at least three operating modes. A first operating mode (e.g., 297) of the at least three operating modes is associated with a first drive voltage, a second operating mode (e.g., 298) of the at least three operating modes is associated with a second drive voltage and a first duty cycle range of the pump, and a third operating mode (e.g., 299) of the at least three operating modes is associated with a second duty cycle range of the pump. The second drive voltage is different from the first drive voltage and the second duty cycle range is different from the first duty cycle range.

In another particular implementation, a system (e.g., 200) includes a wound therapy device (e.g., 210) configured to be worn by a user. The wound therapy device includes a pump (e.g., 150, 278, and/or 279) and a controller (e.g., 260) coupled to the pump. The controller is configured to operate the pump in one of at least three operating modes. A first operating mode (e.g., 297) of the at least three operating modes is associated with a first drive voltage, a second operating mode (e.g., 298) of the at least three operating modes is associated with a second drive voltage and a first duty cycle range, and a third operating mode (e.g., 299) of the at least three operating modes is associated with a second duty cycle range. The second drive voltage is different from the first drive voltage and the second duty cycle range is different from the first duty cycle range. The system also includes a dressing (e.g., 216) configured to be coupled to a wound site and to the wound therapy device.

In another particular implementation, a wound therapy device (e.g., 210) includes a pump (e.g., 150, 278, and/or 279) configured to be worn by a user and a controller (e.g., 260) coupled to the pump and configured to transition the pump from operating in a first operating mode (e.g., 298) to operating in a second operating mode (e.g., 299) responsive to determining a leak counter (e.g., 291) satisfies a leak counter threshold (e.g., 295) or a battery level satisfies a battery level threshold (e.g., 295). The first operating mode is associated with a first duty cycle range that is different from a second duty cycle range associated with the second operating mode.

Thus, FIG. 2A describes system 200 for providing positive-pressure therapy. System 200 may advantageously operate a pump (e.g., reduced-pressure source 278 or positive-pressure source 279) in one of at least three operating modes to improve the flexibility of system 200. For example, operating the pump in first operating mode 297 (e.g., the boost operating mode) may cause the pump to more quickly reach output of a therapeutic level of pressure. Additionally, operation in third operating mode 299 (e.g., the reduced power operating mode) may preserve battery charge for a longer period of time will still providing a therapeutic, albeit lower level, of pressure to tissue site 220. Preserving the battery for a longer time may enable a user of device 210 to fix a leak or to recharge a battery without device 210 powering down (and ceasing to provide pressure to tissue site 220).

Figure 3:
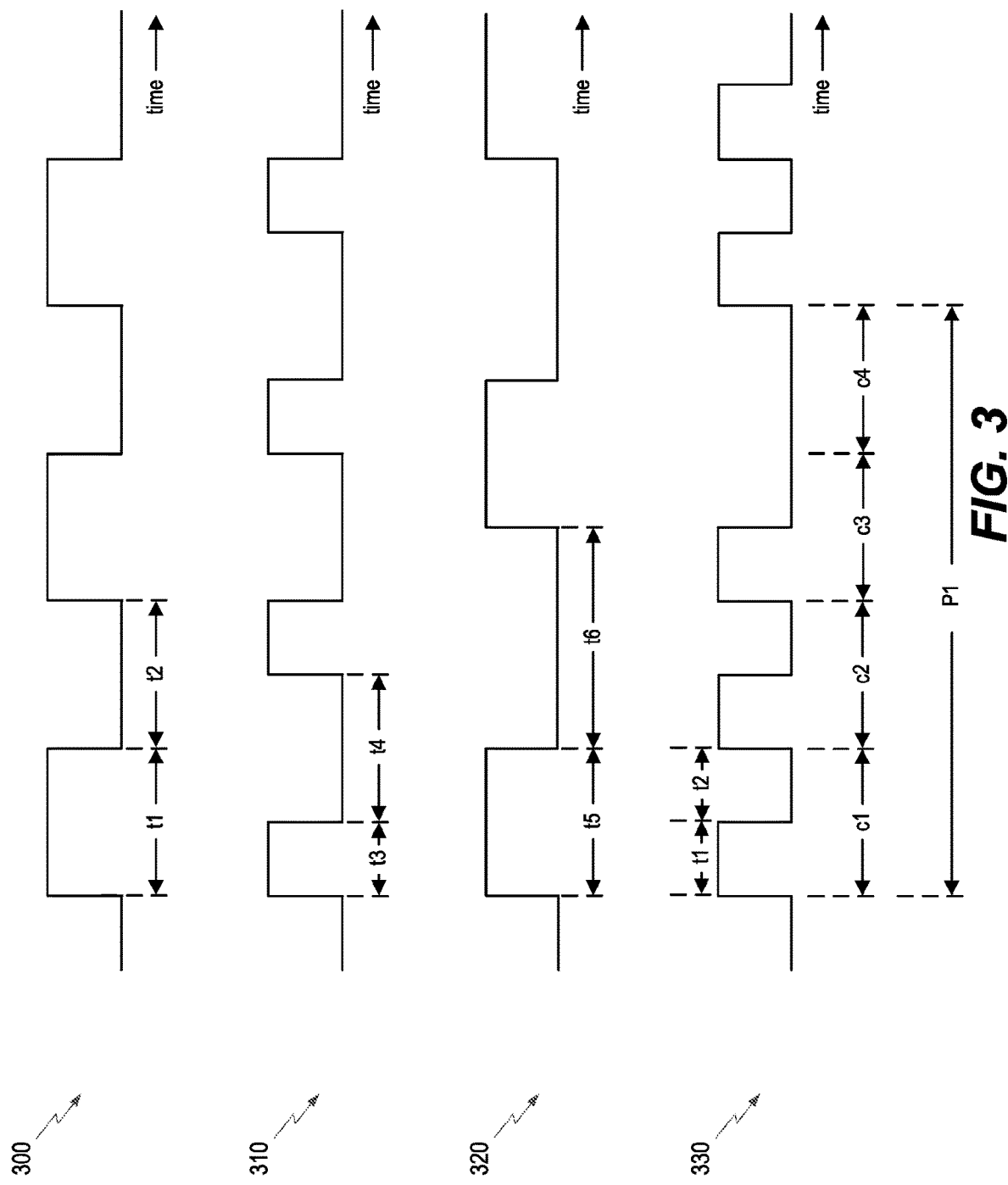
FIG. 3 is a diagram of examples of changing a duty cycle of a pump of a wound therapy device.

FIG. 3 illustrates examples of adjusting (e.g., decreasing) a duty cycle of a pump, such as pump 150, reduced-pressure source 278, and/or positive-pressure source 279. The duty cycle of the pump may be decreased when the pump is transitioned from one operating mode to another operating mode, such as from a normal power operating mode to a reduced power operating mode. Although the changes are illustrated as decrements to the duty cycle, the duty cycle may be increased, such as when transitioning from one operating mode to another operating mode, such as from a reduced power operating mode to a normal power operating mode and/or a normal power operating mode to a boost operating mode. A voltage may also be adjusted (e.g., increased) in addition to adjusting (e.g., increasing) the duty cycle.

FIG. 3 includes a first example 300 of a duty cycle of a pump, such as pump 150, reduced-pressure source 278, and/or positive-pressure source 279. In first example 300, the pump is on (e.g., a drive voltage is applied to the pump) for the same amount of time each period that the pump is off (e.g., no voltage is applied to the pump). For example, the pump is on for a first time t1, the pump is off for a second time t2, and t1 is substantially equal to t2. This pattern is repeated for each period of time of the duty cycle.

FIG. 3 also includes a second example 310 of a duty cycle of the pump. Second example 310 has a reduced duty cycle as compared to first example 300. In second example 310, the amount of time that the pump is on (e.g., the "on-time" of the pump) is reduced. For example, the pump is on for a third time t3, the pump is off for a fourth time t4, and t3 is less than t4 (and t1 and t2). Thus, in second example 310, the amount of time that the pump is on is reduced (e.g., a set time or a maximum allowable on-time for a particular cycle), thereby reducing the overall duty cycle.

FIG. 3 also includes a third example 320 of a duty cycle of the pump. Third example 320 has a reduced duty cycle as compared to first example 300. In third example 320, the amount of time the pump is off (e.g., the "off-time" of the pump) is increased. For example, the pump is on for a fifth time t5 (which is the same as t1 and t2), the pump is off for a sixth time t6, and t6 is greater than t5 (and t1 and t2). Thus, in third example 320, the amount of time that the pump is off is increased, thereby reducing the overall duty cycle.

FIG. 3 further includes a fourth example 330 of a duty cycle of the pump. Fourth example 330 illustrates another technique for reducing the duty cycle of the pump—limiting the cycles per period (P1) that the pump is on. For example, the duty cycle of fourth example 330 includes a threshold or limit on the number of cycles (on-off cycles) that may occur during the period (P1). As illustrated in FIG. 3, a cycle has a time of c (e.g., c1, c2, c3, etc.) and the on and off times are equal (t1=t2), similar to the first example 300. In FIG. 3, the threshold or limit is illustrated has having a value of three cycles within period (P1) and period (P1) is illustrated as four cycles in duration. By reducing the number of cycles (e.g., the number of cycles that the pump is on), the duty cycle of the pump may be reduced. Although limiting a number of cycles over a duration or period is illustrated in the fourth example 330, in other examples, a threshold number of continuous cycle before a delay or cooling of period (duration of c4) may be used to control or adjust duty cycles.

Although FIG. 3 illustrates distinct examples (300-330) of reducing the duty cycle of the pump, one or more of the examples may be combined. For example, the on-time of the pump may be reduced and the off-time of the pump may be increased. Additionally, or alternatively, the on-time may be reduced and the number of cycles may be limited. Thus, any combination of the techniques described with reference to FIG. 3 may be used to reduce the duty cycle of the pump. Additionally, reversing the techniques may be used to increase the duty cycle of the pump. For example, the on-time may be increased, the off-time may be reduced, and/or the number of cycles may be increased to increase the duty cycle.

Figure 4:
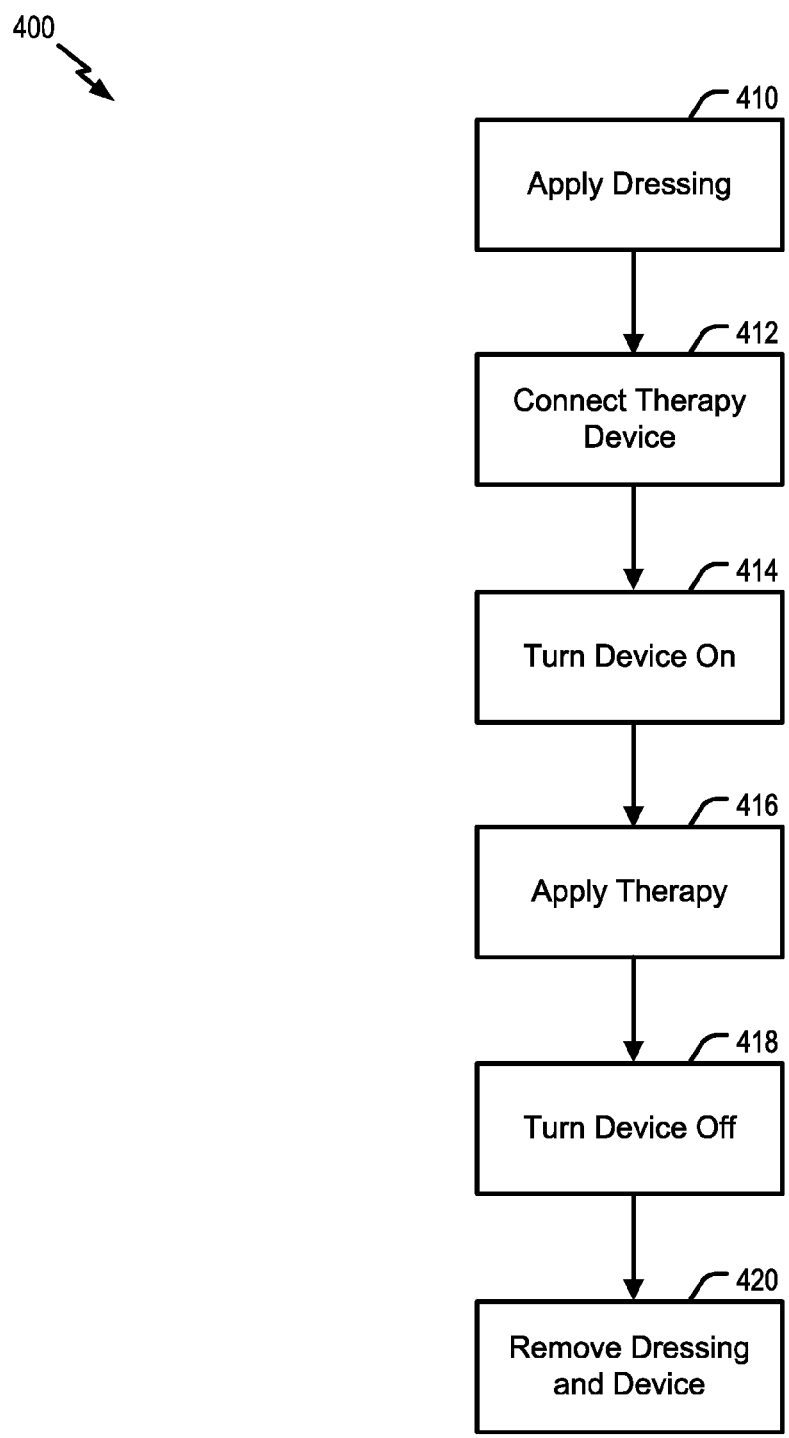
FIG. 4 is a flowchart illustrating an example of a method of using a wound therapy device.

FIG. 4 illustrates a method 400 of using a wound therapy device. Method 400 includes applying a dressing, at 410. For example, the dressing may include or correspond to the dressing 116 or dressing 216. The dressing may be applied to a wound site (e.g., tissue site 120 or tissue site 220) of a user. Method 400 includes connecting the therapy device, at 412. For example, tube 114 or tube 214 may be connected to dressing 116 or dressing 216 and therapy device 110 or device 210. Additionally, one or more batteries may be connected to therapy device 110 or device 210.

Method 400 includes turning the therapy device on, at 414. For example, a power switch may be toggled into an on position. Method 400 includes applying therapy, at 416. For example, a controller (e.g., 260) of the device 210 may cause pump 150, reduced-pressure source 278, or positive-pressure source 279 to apply pressure (e.g., negative pressure or positive pressure) to the wound site. Applying the therapy may include the controller operating pump 150 in one or more different operating modes, as further described with reference to FIG. 5.

Method 400 includes turning the device off, at 418. For example, when therapy is complete, the therapy device may be turned off, such as be toggling a power switch into an off position. Method 400 further includes removing the dressing and the therapy device, at 420. For example, the dressing may be unattached from the wound site and the therapy device may be disconnected from the dressing.

Figure 5:
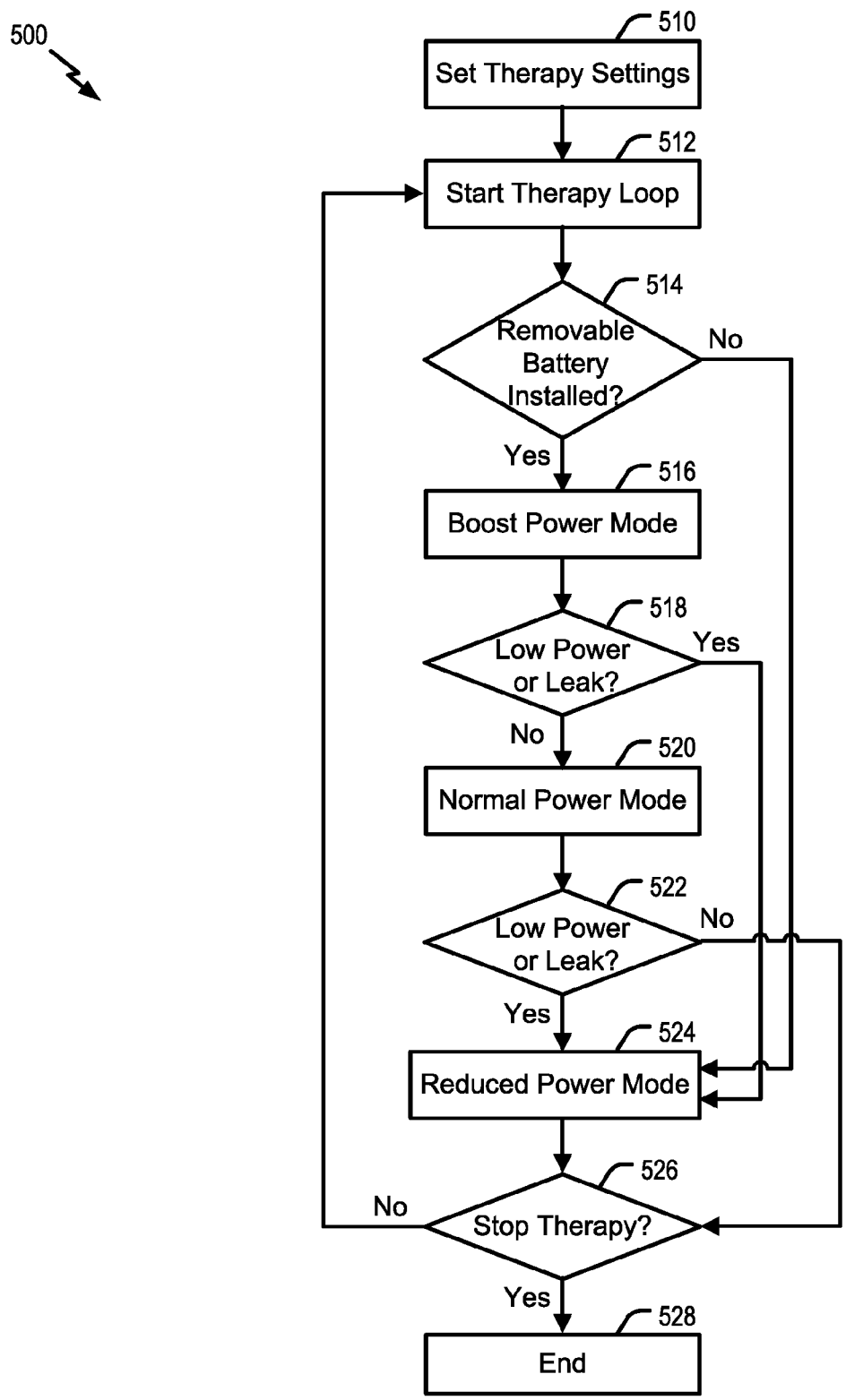
FIG. 5 is a flowchart illustrating an example of a method of operating a pump of a wound therapy device in one of multiple operating modes.

FIG. 5 illustrates a method 500 of operating a pump of a wound therapy device in one of multiple operating modes. In a particular implementation, method 500 is performed by controller 260. In a particular implementation, method 500 corresponds to operation 416 of FIG. 4.

Method 500 includes setting therapy settings, at 510. For example, a controller (e.g., 260) may load a set of pre-stored settings from a memory. Additionally, or alternatively, the settings may be received from a user (e.g., via a user input device or a separate mobile device, such as a cell phone). Method 500 includes starting the therapy loop, at 512. For example, the controller (e.g., 260) may load (or receive) the settings and start the loop when the therapy device is powered on.

Method 500 also includes determining whether a removable battery is installed, at 514. For example, in some implementations, the therapy device may include two batteries, one of which is removable (and rechargeable). In such implementations, the controller may determine whether the removable/rechargeable battery is connected to the therapy device. In implementations in which a single, non-removable battery is used, operation 514 is skipped or omitted.

If the removable battery is present (or if operation 514 is skipped), method 500 proceeds to 516, and a boost operating mode is initiated. For example, the controller may send one or more control signals to pump 150 to operate pump 150 a boost operating mode. The boost operating mode is associated with a first drive voltage of pump 150. The boost operating mode may enable the pump and/or the dressing to more quickly reach a therapeutic pressure than other operating modes, but may consume more voltage, thereby draining the batteries of the therapy device faster. Accordingly, the boost operating mode may be used for a limited time upon power-on. The boost operating mode is further described with reference to FIG. 6.

Method 500 then continues to 518, and it is determined whether a leak situation or a low power situation is occurring. For example, a leak counter (e.g., 291) may be compared to a leak threshold, and if the leak counter satisfies the leak threshold, a leak condition is occurring (e.g., dressing 116 or 216 may have become partially uncoupled from the wound site or there may be a hole or other leak in one of the components of the therapy device). Additionally, a battery level of one or more batteries of the therapy device may be compared to a battery threshold, and if the battery level fails to satisfy the battery threshold, a low power condition is occurring. If either (or both) a leak condition or a low power condition is detected, method 500 proceeds to 524, and a reduced power operating mode is initiated. For example, the controller may send one or more control signals to pump 150 to operate pump 150 in a reduced power operating mode. The reduced power operating mode is further described with reference to FIG. 8.

If neither a leak condition nor a low power condition is detected, method 500 continues to 520, and a normal power operating mode is initiated. For example, the controller may send one or more control signals to pump 150 to operate pump 150 in a normal power operating mode. The normal power operating mode is associated with a second drive voltage of pump 150 that is different from the first drive voltage. In a particular implementation, the second drive voltage is less than the first drive voltage (associated with the boost operating mode). The normal power operating mode is also associated with a first duty cycle range of pump 150. The normal power operating mode is further described with reference to FIG. 7. After initiating the normal power operating mode, method 500 continues to 522.

At 522, it is determined whether a leak condition or a low power condition is occurring. If either a leak condition or a low power condition is detected, method 500 continues to 524, and the reduced power operating mode is initiated. The reduced power operating mode is associated with a second duty cycle range of pump 150 that is different from the first duty cycle range (associated with the normal power operating mode). In a particular implementation, the second duty cycle range is less (e.g., includes at least some smaller values) than the first duty cycle range. After operating in the reduced power operating mode, method 500 continues to 526.

Returning to 514, if the removable battery is not detected, method 500 proceeds to 520, and the reduced power operating mode is initiated. For example, the reduced power operating mode may be initiated to preserve battery power of the non-removable battery until the removable battery is connected. In some implementations, the removable battery may store more charge and be used as the primary source of power when connected, with the non-removable battery acting as a backup. Operating in the reduced power operating mode may enable some degree of therapy to be provided while preserving more power than operating in the normal power operating mode.

Returning to 522, if neither a leak condition nor a low power condition is detected, method 500 proceeds to 526, and it is determined if therapy is to stop. For example, the controller may detect that a user has pressed a stop button on the therapy device. If an end of therapy is determined, method 500 terminates at 528. Alternatively, if therapy is not stopped, method 500 returns to 512, and the loop begins again.

Thus, method 500 enables a controller to operate a pump of a therapy device in multiple different operating modes in multiple different conditions. For example, pump 150 may be operated in the boost operating mode upon power-on to quickly reach a therapeutic pressure output. Additionally, pump 150 may be operated in the normal power operating mode under normal conditions to provide a target pressure. If a leak condition or a low power condition is detected, the pump may be operated in the reduced power operating mode to provide some level of pressure while preserving battery charge until a user can fix the leak or recharge (or replace) the batteries. Thus, method 500 enables operation of the therapy device for longer time periods than conventional therapy devices.

Figure 6:
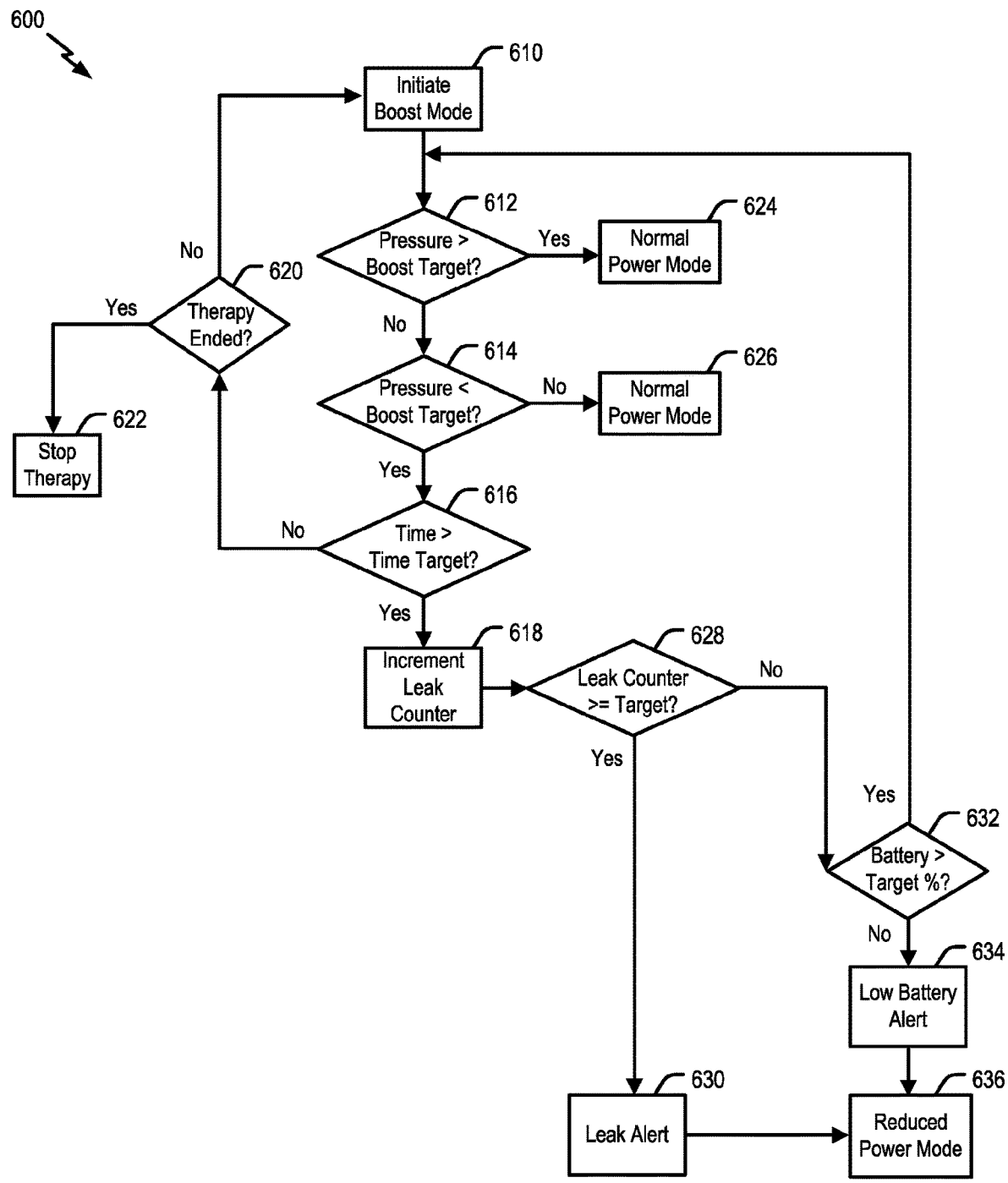
FIG. 6 is a flowchart illustrating an example of a method of operating a pump of a wound therapy device in a boost operating mode.

FIG. 6 illustrates a method 600 of operating a pump of a wound therapy device in a boost operating mode. In a particular implementation, method 600 is performed by controller 260. In a particular implementation, method 600 corresponds to operation 516 of FIG. 5.

Method 600 includes initiating boost operating mode, at 610. For example, a particular drive voltage associated with the boost operating mode may be applied to pump 150. In a particular implementation, the particular drive voltage is 18 volts. In other implementations, the particular drive voltage associated with the boost operating mode is greater than or less than 18 volts.

Method 600 includes determining whether the pressure applied by (e.g., provided by) pump 150 is above a boost target pressure, at 612. For example, the controller may receive pressure data from a pressure sensor (e.g., 272, 274) of the therapy device. The pressure data indicates the pressure detected from pump 150. The controller may compare the pressure to the boost target pressure (e.g., a threshold) to determine if the pressure is greater than the boost target pressure. In a particular implementation, the boost target pressure is 75 mm Hg.

If the pressure is greater than the boost target pressure, the boost operating mode is determined to be successful (e.g., a therapeutic pressure has been reached), and the controller transitions pump 150 in the normal power operating mode, at 624. Operating pump 150 in the normal power operating mode may use a lower drive voltage, which conserves battery charge as compared to operating in the boost operating mode. The lower drive voltage may be a designed drive voltage or a minimum operating drive voltage. Additionally, the first drive voltage may be an overvoltage, a maximum operating drive voltage, or a conditional maximum operating drive voltage (e.g., a maximum voltage for "X" amount of time). If the pressure is not greater than the boost target pressure (e.g., the pressure is less than or equal to the boost target pressure), method 600 continues to 614.

Method 600 includes determining whether the pressure is less than the boost target pressure, at 614. If the pressure is not less than the boost target pressure (e.g., the pressure is equal to the boost target pressure), then the controller transitions pump 150 to the normal power operating mode, at 626. If the pressure is less than the boost target pressure, method 600 continues to 616.

Method 600 includes determining whether an elapsed time (e.g., a time since the boost operating mode was initiated) satisfies (e.g., is greater than) a time target (e.g., a threshold), at 616. In a particular implementation, the time target is 60 seconds. In other implementations, the time target is less than 60 or more than 60 seconds, such as 30 seconds, 45 seconds, 90 seconds, 120 seconds, or 240 seconds, as non-limiting examples.

If the elapsed time is not greater than the target time (e.g., the elapsed time is less than or equal to the target time), method 600 proceeds to 620, and it is determined whether the therapy is to be ended. For example, the therapy may be determined to be ended if the controller detects that a user has pressed a stop button on the therapy device. If the therapy is determined to be ended, method 600 proceeds to 622, and therapy is stopped (e.g., pump 150 is powered down). If therapy is determined to continue, method 600 returns to 610, and boost operating mode is initiated.

Returning to 616, if the elapsed time is greater than the target time, method 600 continues to 618, and a leak counter is incremented. For example, the controller may maintain a leak counter to count the number of detected leak events. The leak counter may be initialized to zero when the settings for the therapy device are set on power-on. Because one or two leak events may be false positives (or due to motion of the user), a leak is not indicated until a threshold number of leak events are detected. To illustrate, method 600 proceeds to 628, and it is determined if the leak counter satisfies (e.g., is greater than or equal to) a leak target. In a particular implementation, the leak target is five, such that five leak events are detected before a leak is indicated and actions are taken. In other implementations, the leak target may be fewer than five or more than five.

If the leak counter satisfies the leak target, method 600 continues to 630, and a leak alert is initiated. For example, an indicator of the therapy device may be turned on. The indicator may be visual (e.g., a light), auditory, haptic, or a combination thereof. Additionally, or alternatively, a leak alert message can be wirelessly transmitted to a mobile device of the user, such as a mobile phone that is executing an application associated with the therapy device, and the leak alert can be displayed at the mobile device. After the leak alert is initiated, method 600 proceeds to 636, and the controller transitions pump 150 to the reduced power operating mode.

Returning to 628, if the leak counter does not satisfy the leak target (e.g., the leak counter is less than the leak target), method 600 proceeds to 632, and it is determined whether a battery level of one or more batteries of the therapy device is greater than a target % (e.g., a target battery level). In a particular implementation, the target battery level is 25%. In other implementations, the target battery level is less than or greater than 25%, such as 15%, 30%, or 40%, as non-limiting examples.

If the battery level is greater than the target battery level, the controller continues to operate pump 150 in the boost operating mode, and method 600 returns to 612. If the battery level is less than or equal to the target battery level, method 600 continues to 634, and a low battery alert is initiated. For example, an indicator of the therapy device may be turned on. The indicator may be visual (e.g., a light), auditory, haptic, or a combination thereof. Additionally or alternatively, a low battery alert message can be wirelessly transmitted to a mobile device of the user, such as a mobile phone that is executing an application associated with the therapy device, and the low battery alert can be displayed at the mobile device. After the low battery alert is initiated, method 600 continues to 636, and the controller transitions pump 150 to the reduced power operating mode.

Thus, FIG. 6 describes a method for operating a pump of a therapy device in a boost operating mode. Operating the pump in the boost operating mode may more quickly establish a therapeutic amount of pressure output by the pump. The pump may be operated in the boost operating mode upon power-on for a limited amount of time (e.g., until a target pressure is reached) so as not to deplete battery charge too quickly. Additionally, or alternatively, the boost operating mode may be activated responsive to user input or based on detecting AC power (e.g., plugged into a power source or a power grid), the one or more batteries are charging, or a combination thereof.

Figure 7:
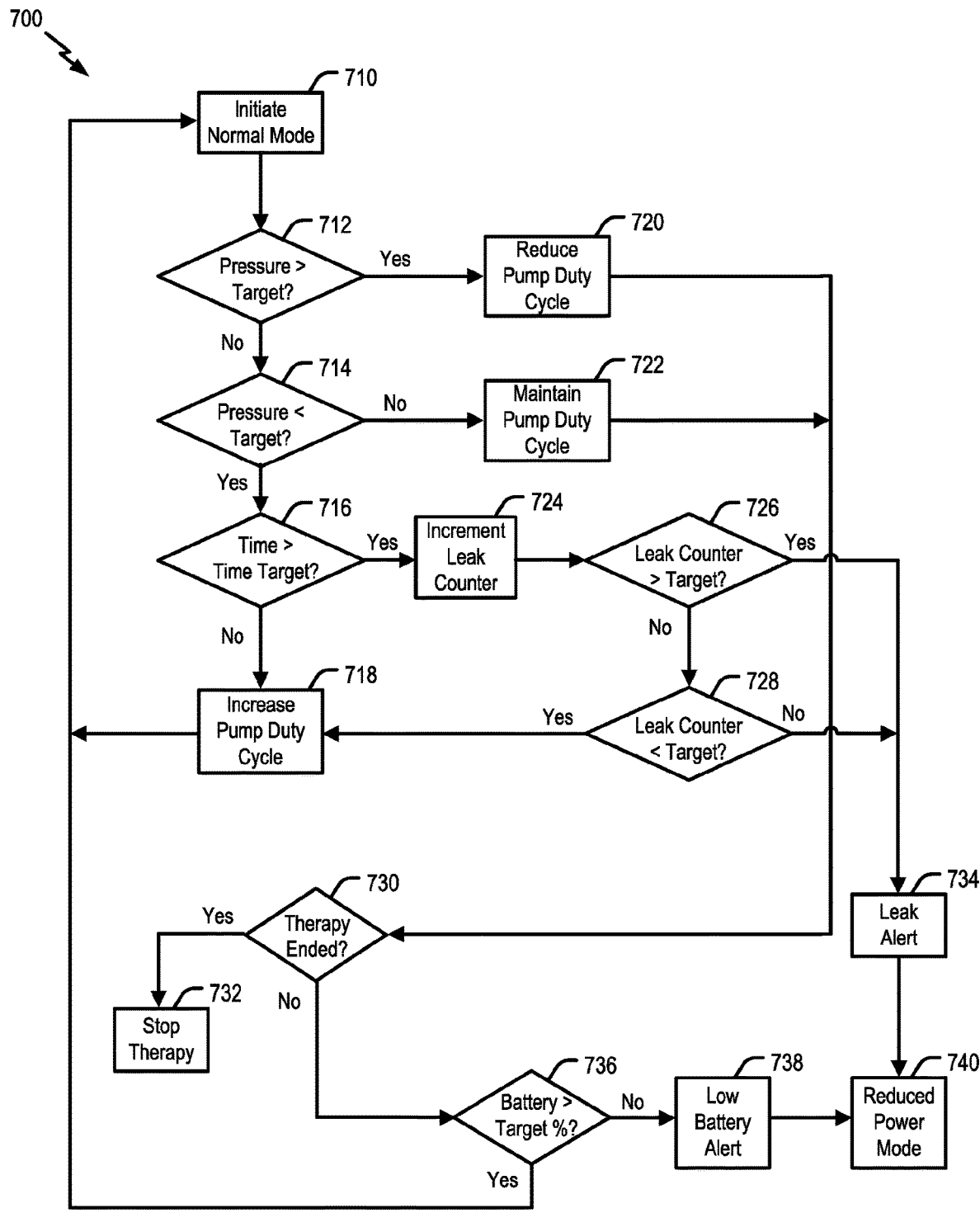
FIG. 7 is a flowchart illustrating an example of a method of operating a pump of a wound therapy device in a normal power operating mode.

FIG. 7 illustrates a method 700 of operating a pump of a wound therapy device in a normal power operating mode. In a particular implementation, method 700 is performed by controller 260. In a particular implementation, method 700 corresponds to operation 520 of FIG. 5.

Method 700 includes initiating normal power operating mode, at 710. For example, the controller may supply pump 150 with a particular drive voltage. The particular drive voltage may be different from the drive voltage associated with the boost operating mode. In a particular implementation, the particular drive voltage is 15 volts. In such an implementation, the instantaneous current is approximately 50-60 milli-amps. In other implementations, the particular drive voltage is less than or greater than 15 volts. The normal power operating mode may also be associated with a particular duty cycle range of pump 150. In a particular implementation, the particular duty cycle range may be 50%-80%. In other implementations, the particular duty cycle range may have other values, such as 40%-60%, 50%-75%, or 60%-90%, as non-limiting examples. The particular duty cycle range may be associated with a particular range of pressure output by pump 150 or a particular range of therapeutic pressure at the dressing established by pump 150. For example, the particular duty cycle range may result in pressures of 100 to 150 mm Hg at the dressing, as a non-limiting example. In other implementations, the range of pressures may have other values, such as 115 to 135 mm Hg, as another non-limiting example.

Method 700 includes determining whether pressure applied by pump 150 is greater than a target pressure, at 712. For example, the controller may receive pressure data from a pressure sensor (e.g., 272, 274) of the therapy device. The pressure data may indicate the pressure output by pump 150, and the controller may compare the pressure to a target pressure (e.g., a threshold). In a particular implementation, the target pressure is 125 mm Hg. In other implementations, the target pressure is less than or greater than 125 mm Hg.

If the pressure is greater than the target pressure, method 700 proceeds to 720, and the duty cycle of pump 150 is reduced. After reducing the duty cycle, method 700 proceeds to 730. Returning to 712, if the pressure is not greater than the target pressure (e.g., the pressures is less than or equal to the target pressure), method 700 continues to 714, and it is determined if the pressure is less than the target pressure. If the pressure is not less than the target pressure (e.g., the pressure is equal to, or substantially equal to, the target pressure), method 700 proceeds to 722, and the duty cycle of pump 150 is maintained at the current value. Method 700 then proceeds to 730.

At 730, it is determined whether therapy is to be ended. If therapy is to be ended, method 700 proceeds to 732, and therapy is stopped. If therapy is not to be ended, method 700 proceeds to 736, and it is determined if a battery level of one or more batteries of the therapy device is greater than a target % (e.g., a target battery level). In a particular implementation, the target battery level is 25%. In other implementations, the target battery level is less than or greater than 25%, such as 15%, 30%, or 40%, as non-limiting examples. If the battery level is greater than the target battery level, method 700 returns to 710 and operation of pump 150 in the normal power operating mode continues. If the battery level is less than or equal to the target battery level, method 700 proceeds to 738, and a low battery alert is initiated, as described with reference to FIG. 6. Method 700 then proceeds to 740, and the controller transitions pump 150 into the reduced power operating mode.

Returning to 714, if the pressure is less than the target pressure, method 700 continues to 716, and it is determined if an elapsed time since initiation of the normal power operating mode is greater than a time target (e.g., a threshold). In a particular implementation, the time target is 60 seconds. In other implementations, the time target is less than 60 or more than 60 seconds, such as 30 seconds, 45 seconds, 90 seconds, 120 seconds, or 240 seconds, as non-limiting examples.

If the elapsed time is greater than the time target, method 700 continues to 718, and the duty cycle of pump 150 is increased. Method 700 then returns to 710, and operation in the normal power operating mode is continued. If the elapsed time is not greater than the time target (e.g., the elapsed time is less than or equal to the time target), method 700 proceeds to 724, and a leak counter is incremented. For example, the controller may maintain the leak counter to track a number of leak events detected by the controller, as described with reference to FIG. 6. After incrementing the leak counter, method 700 continues to 726.

Method 700 includes determining whether the leak counter is greater than a leak target (e.g., a threshold), at 726. If the leak counter is greater than the leak target, method 700 proceeds to 734, and a leak alert is initiated, as described with reference to FIG. 6. Method 700 then proceeds to 740, and the controller transitions pump 150 into the reduced power operating mode. Returning to 726, if the leak counter is not greater than the leak target, method 700 continues to 728, and it is determined if the leak counter is less than the leak target. If the leak counter is not less than the leak target (e.g., the leak counter is equal to the leak target), method 700 proceeds to 734, and a leak alert is initiated, as described with reference to FIG. 6. Method 700 then proceeds to 740, and the controller transitions pump 150 into the reduced power operating mode.

Returning to 728, if the leak counter is less than the leak target, method 700 proceeds to 718, and the duty cycle of pump 150 is increased. Method 700 then returns to 710, and operation continues in the normal power operating mode.

Thus, FIG. 7 describes a method of operating a pump of a therapy device in a normal power operating mode. Operating the pump in the normal power operating mode may supply a therapeutic amount of pressure to a wound site as part of therapy for the wound site.

Figure 8:
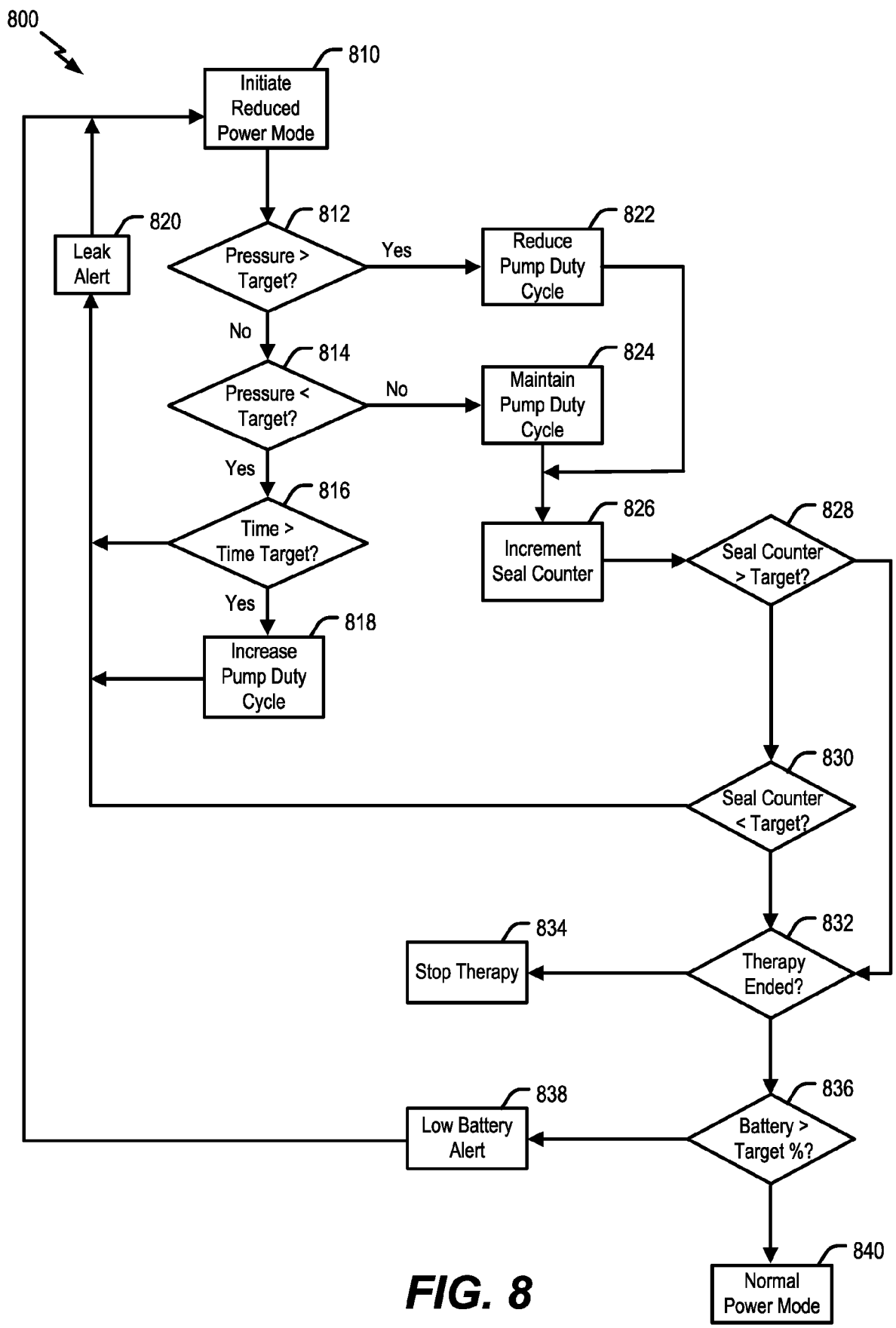
FIG. 8 is a flowchart illustrating an example of a method of operating a pump of a wound therapy device in a reduced power operating mode.

FIG. 8 illustrates a method 800 of operating a pump of a wound therapy device in a reduced power operating mode. In a particular implementation, method 800 is performed by controller 260. In a particular implementation, method 800 corresponds to operation 524 of FIG. 5.

Method 800 includes initiating reduced power operating mode, at 810. For example, the controller may supply pump 150 with a particular drive voltage. The particular drive voltage may be different from the drive voltage associated with the boost operating mode. In a particular implementation, the particular drive voltage is 15 volts. In other implementations, the particular drive voltage is less than or greater than 15 volts. The reduced power operating mode may also be associated with a particular duty cycle range of pump 150. The particular duty cycle range may be different from the duty cycle range associated with the normal power operating mode. In a particular implementation, the particular duty cycle range may be 10%-40%. In other implementations, the particular duty cycle range may have other values, such as 5%-25%, 25%-40%, or 30%-50%, as non-limiting examples. The particular duty cycle range may be associated with a particular range of pressure output by pump 150. For example, the particular duty cycle range may result in pressures of 50 to 100 mm Hg, as a non-limiting example. In other implementations, the range of pressures may have other values, such as 65 to 85 mm Hg, as another non-limiting example.

Method 800 includes determining whether pressure output by pump 150 is greater than a target pressure, at 812. For example, the controller may receive pressure data from a pressure sensor of the therapy device. The pressure data may indicate the pressure output by pump 150, and the controller may compare the pressure to a target pressure (e.g., a threshold). In a particular implementation, the target pressure is 75 mm Hg. In other implementations, the target pressure is less than or greater than 75 mm Hg.

If the pressure is greater than the target pressure, method 800 proceeds to 822 and a duty cycle of pump 150 is reduced. Method 800 then proceeds to 826. If the pressure is not greater than the target pressure (e.g., the pressure is less than or equal to the target pressure), method 800 continues to 814, and it is determined if the pressure is less than the target pressure. If the pressure is not less than the target pressure (e.g., the pressure is equal to, or substantially equal to the target pressure), method 800 proceeds to 824, and the duty cycle of pump 150 is maintained. Method 800 then proceeds to 826.

At 826, a seal counter is incremented. For example, the controller may maintain a seal counter to track a number of seal events detected by the controller. Because one or two seal events may be false positives (or insufficient to fully fix a leak), the controller may compare the number of seal events to a threshold before transitioning pump 150 from the reduced power operating mode. To illustrate, after incrementing the seal counter, method 800 continues to 828, and it is determined if the seal counter is greater than a seal target (e.g., a threshold). If the seal counter is greater than the seal target, method 800 proceeds to 832. If the seal counter is not greater than the seal target (e.g., the seal counter is less than or equal to the seal target), method 800 continues to 830, and it is determined if the seal count is less than the seal target. If the seal count is not less than the seal target (e.g., if the seal count is equal to the seal target), method 800 continues to 832.

Method 800 includes determining whether therapy is to be ended, at 832. For example the controller may determine that therapy is to be ended based on detecting the user press a stop or cancel button on the therapy device. If therapy is to be ended, method 800 proceeds to 834 and therapy is stopped. If therapy is to continue, method 800 proceeds to 836, and a battery level of one or more batteries of the therapy device is compared to a target % (e.g., a target battery level). In a particular implementation, the target battery level is 25%. In other implementations, the target battery level is less than or greater than 25%, such as 15%, 30%, or 40%, as non-limiting examples. If the battery level is greater than the target level, method 800 proceeds to 840, and the controller transitions pump 150 into the normal power operating mode. If the battery level is not greater than the target level, method 800 proceeds to 838, and a low battery alert is initiated, as described with reference to FIG. 6. Method 800 then returns to 810, and operation in the reduced power operating mode continues.

Returning to 830, if the seal counter is less than the seal target, method 800 proceeds to 820, and a leak alert is initiated, as described with reference to FIG. 6. Method 800 then returns to 810, and operation in the reduced power operating mode continues.

Returning to 814, if the pressure is less than the target pressure, method 800 continues to 816, and it is determined if an elapsed time since entering into the reduced power operating mode is greater than a time target (e.g., a threshold). In a particular implementation, the time target is 60 seconds. In other implementations, the time target is less than 60 or more than 60 seconds, such as 30 seconds, 45 seconds, 90 seconds, 120 seconds, or 240 seconds, as non-limiting examples. If the elapsed time is not greater than the time target, method 800 proceeds to 820, and the leak alert is initiated. Method 800 then returns to 810. If the elapsed time is greater than the time target, method 800 continues to 818, and a duty cycle of pump 150 is increased. Method 800 then proceeds to 820, and the leak alert is initiated. Method 800 then returns to 810, and operation in the reduced power operating mode continues.

Thus, FIG. 8 describes a method of operating a pump of a therapy device in a reduced power operating mode. Operating the pump in the reduced power operating mode may supply less, but still a therapeutic level, of pressure than a normal power operating mode. However, operating the pump in the reduced power operating mode conserves battery charge as compared to other operating modes. Operation in the reduced power operating mode may continue until a seal is detected (e.g., a leak is fixed) or a sufficient battery level is detected (or a removable battery is reattached).

Figure 9:
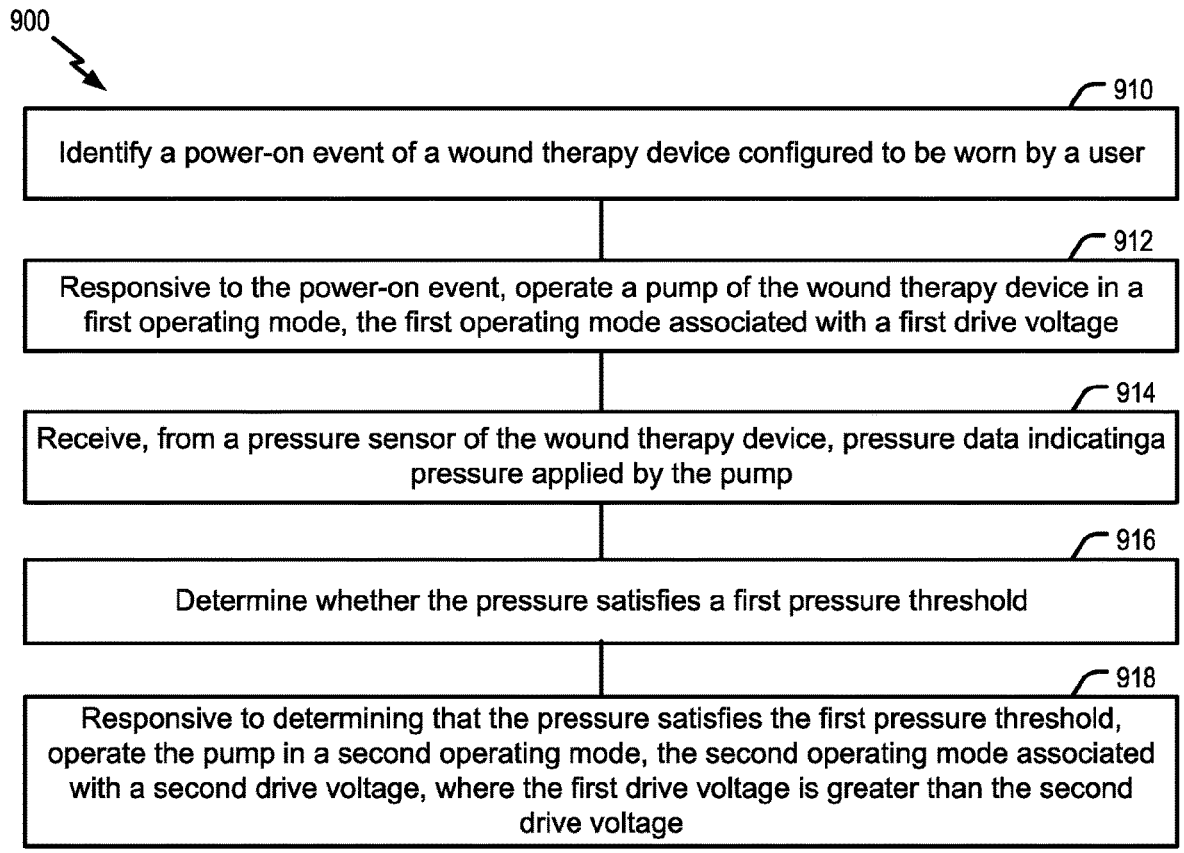
FIG. 9 is a flowchart illustrating an example of a method of operating a pump of a wound therapy device.

FIG. 9 illustrates a method 900 of operating a pump of a wound therapy device. Method 900 may be performed at or by system 100 or 200, and/or by controller 260. Method 900 includes identifying a power-on event of a wound therapy device, at 910. The wound therapy device is configured to be worn by a user. For example, controller 260 of device 210 may detect a power-on event.

Method 900 also includes, responsive to the power-on event, operating a pump of the wound therapy device in a first operating mode, at 912. The first operating mode is associated with a first drive voltage. For example, controller 260 may operate pump 150, reduced-pressure source 278, positive-pressure source 279, or a combination thereof in first operating mode 297. In some implementations, operating the pump in the first operating mode includes sending one or more control signals indicating the first operating mode to the pump. Additionally, or alternatively, operating the pump in the first operating mode includes adjusting a drive voltage applied to the pump.

Method 900 includes receiving, from a pressure sensor of the wound therapy device, pressure data indicating a pressure applied by the pump, at 914. For example, controller 260 receives, from first pressure sensor 272 and/or second pressure sensor 274, pressure data indicating an amount of pressure applied by pump 150. To illustrate, the pressure indicated corresponds to pressure at a wound site or within dressing 116. One or more lumens (e.g., sense lumens) may provide a pressure sensor of the therapy device with pressure from the dressing 116 such that the pressure sensor generates a pressure reading of therapeutic pressure.

Method 900 also includes determining whether the pressure satisfies a first pressure threshold, at 916. For example, controller 260 may compare the pressure to one of the one or more thresholds 295.

Method 900 further includes, responsive to determining that the pressure satisfies the first pressure threshold, operating the pump in a second operating mode, at 918. The second operating mode is associated with a second drive voltage. The first drive voltage is greater than the second drive voltage. For example, controller 260 may operate pump 150 in second operating mode 298, which is associated with a lower drive voltage than first operating mode 297.

In some implementations, method 900 includes receiving, from the pressure sensor, second pressure data indicating a second pressure applied by the pump, comparing the second pressure to a second pressure threshold, and, responsive to determining that the second pressure is greater than the second pressure threshold, reducing a duty cycle of the pump. For example, responsive to pressure data from first pressure sensor 272 and/or second pressure sensor 274, controller 260 may reduce a duty cycle of pump 150. Method 900 may also include, determining whether a battery level of the wound therapy device satisfies a battery threshold and, responsive to the battery level satisfying the battery threshold, continuing to operate the pump in the second operating mode. For example, if the battery level of device 210 satisfies the battery threshold, controller 260 continues to operate pump 150 in second operating mode 298. In some such implementations, method 900 further includes, responsive to the battery level failing to satisfy the battery threshold, initiating a low battery alert and operating the pump in a third operating mode. The second operating mode is associated with the first duty cycle range of the pump and the third operating mode is associated with a second duty cycle range of the pump that is different from the first duty cycle range. For example, responsive to the battery level failing to satisfy the battery level threshold, controller 260 initiates a low power alert and transitions pump 150 into third operating mode 299.

In some such implementations, method 900 includes, responsive to determining that the second pressure is less than the second pressure threshold, determining whether a time since entering the second operating mode satisfies a time threshold and, responsive to determining that the time does not satisfy the time threshold, increasing a duty cycle of the pump. For example, controller 260 may increase the duty cycle of pump 150 responsive to determining that the time does not satisfy the time threshold. Method 900 may further include continuing to operate the pump in the second operating mode. For example, controller 260 may continue to operate pump 150 in second operating mode 298.

Alternatively, method 900 may include, responsive to determining that the time satisfies the time threshold, incrementing a leak counter and determining whether the leak counter satisfies a threshold. For example, controller 260 may increment leak counter 291. In some such implementations, method 900 further includes, responsive to determining that the leak counter does not satisfy the leak threshold, increasing the duty cycle of the pump and continuing to operate the pump in the second operating mode. For example, controller 260 may increase the duty cycle of pump 150 and continue to operate pump 150 in second operating mode 298. Alternatively, method 900 may further include, responsive to determining that the leak counter satisfies the leak threshold, initiating a leak alert and operating the pump in a third operating mode. The second operating mode is associated with a first duty cycle range of the pump and the third operating mode is associated with a second duty cycle range of the pump that is different from the first duty cycle range. For example, controller 260 may initiate a leak alert and transition pump 150 to third operating mode 299.

Thus, method 900 describes operating a pump in at least two operating modes. The at least two operating modes provide benefits as compared to conventional pumps that operate in a single operating mode. For example, operating in the first operating mode may enable the pump to more quickly output a therapeutic amount of pressure.

Figure 10:
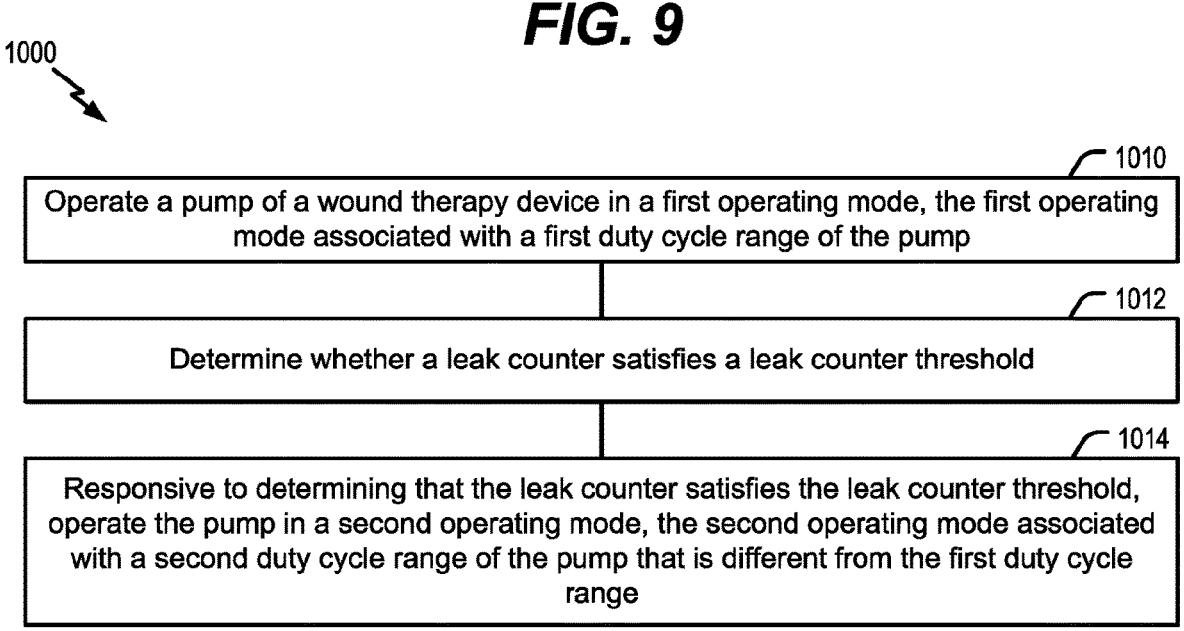
FIG. 10 is a flowchart illustrating an example of another method of operating a pump of a wound therapy device.

FIG. 10 illustrates a method 1000 of operating a pump of a wound therapy device. Method 1000 may be performed at or by system 100 or 200, and/or by controller 260. Method 1000 includes operating a pump of a wound therapy device in a first operating mode, at 1010. The first operating mode is associated with a first duty cycle range of the pump. For example, controller 260 may operate pump 150, reduced-pressure source 278, positive-pressure source 279, or a combination thereof, in second operating mode 298.

Method 1000 also includes determining whether a leak counter satisfies a leak counter threshold, at 1012. For example, controller 260 may determine whether leak counter 291 satisfies a leak counter threshold.

Method 1000 further includes, responsive to determining that the leak counter satisfies the leak counter threshold, operating the pump in a second operating mode, at 1014. The second operating mode is associated with a second duty cycle range of the pump that is different from the first duty cycle range. For example, controller 260 may operate pump 150 in third operating mode 299, which is associated with a duty cycle range that is different from the duty cycle range associated with second operating mode 298. In a particular implementation, the second duty cycle range is less than the first duty cycle range (e.g., the second duty cycle range includes at least some values that are less than the values included in the first duty cycle range).

In some implementations, method 1000 includes receiving, from a pressure sensor, pressure data indicating a pressure applied by the pump and determining whether the pressure is greater than a pressure threshold. For example, controller 260 may receive pressure data from first pressure sensor 272 and/or second pressure sensor 274. In some such implementations, method 1000 includes, responsive to determining that the pressure is greater than the pressure threshold, reducing a duty cycle of the pump and incrementing a seal counter. For example, if the pressure is greater than the pressure threshold, controller 260 reduces the duty cycle of pump 150. In some such implementations, method 1000 further includes determining whether the seal counter satisfies a seal threshold and, responsive to the seal counter failing to satisfy the seal threshold, initiating a leak alert and continuing to operate the pump in the second operating mode. For example, responsive to seal counter 292 failing to satisfy a seal threshold, controller 260 initiates a leak alert and continues to operate pump 150 in third operating mode 299. Alternatively, method 1000 may include, responsive to the seal counter satisfying the seal threshold, determining whether a battery level of one or more batteries of the wound therapy device satisfies a battery threshold and, responsive to the battery level satisfying the battery threshold, operating the pump in the first operating mode. For example, if seal counter 292 satisfies the seal threshold and the battery level satisfies a battery threshold, controller 260 operates pump 150 in second operating mode 298. Alternatively, method 1000 may further include, responsive to the battery level failing to satisfy the battery threshold, initiating a low battery alert and continuing to operate the pump in the second operating mode. For example, if the battery level fails to satisfy the battery threshold, controller 260 initiates a low battery alert and continues to operate pump 150 in third operating mode 299.

Alternatively, method 1000 may include, responsive to determining that the pressure is equal to the pressure threshold, maintaining a duty cycle of the pump and incrementing a seal counter. For example, controller 260 maintains the duty cycle of pump 150 and increments seal counter 292. Alternatively, method 1000 may include, responsive to determining that the pressure is less than the pressure threshold, determining whether a time since entry of the second operating mode satisfies a time threshold and, responsive to determining that the time fails to satisfy the time threshold, initiating a leak alert and continuing to operate the pump in the second operating mode. For example, controller 260 determines that the elapsed time fails to satisfy the time threshold and initiates a leak alert and continues to operate pump 150 in third operating mode 299. Alternatively, method 1000 may further include, responsive to determining that the time satisfies the time threshold, increasing a duty cycle of the pump, initiating a leak alert, and continuing to operate the pump in the second operating mode. For example, controller 260 increases the duty cycle of pump 150, initiates a leak alert, and continues to operate pump 150 in the third operating mode 299.

Thus, method 1000 describes operating a pump in at least two operating modes. The at least two operating modes provide benefits as compared to conventional pumps that operate in a single operating mode. For example, operating in the second operating mode (e.g., a reduced power operating mode) may provide a lesser amount, but still a therapeutic amount, of pressure from the pump while extending the battery life of the wound therapy device.

Figure 11:
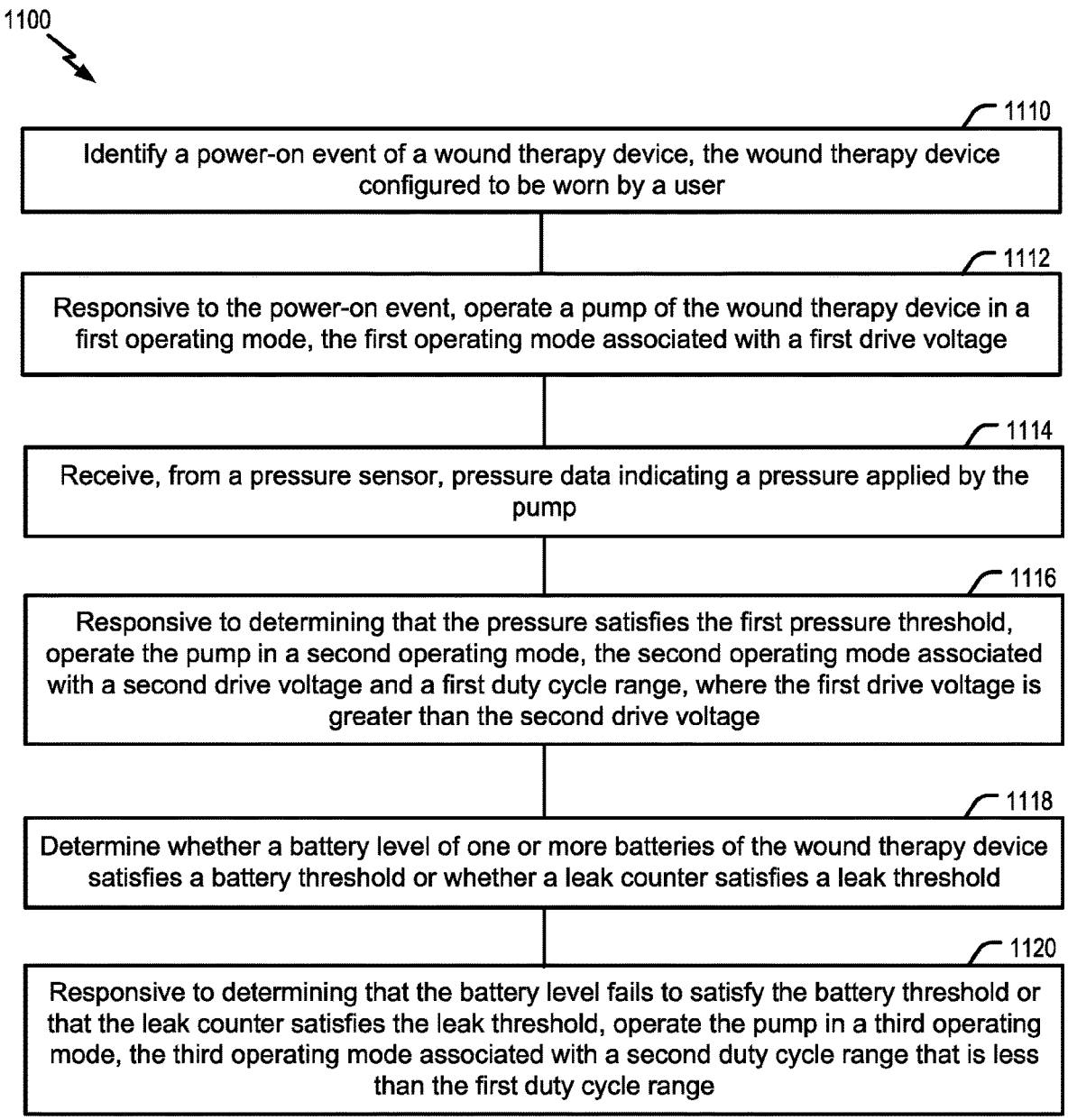
FIG. 11 is a flowchart illustrating an example of another method of operating a pump of a wound therapy device.

FIG. 11 illustrates a method 1100 of operating a pump of a wound therapy device. Method 1100 may be performed at or by system 100, system 200, and/or by controller 260. Method 1100 includes identifying a power-on event of a wound therapy device, at 1110. The wound therapy device is configured to be worn by a user. For example, controller 260 detects a power-on event of device 210.

Method 1100 also includes, responsive to the power-on event, operating a pump of the wound therapy device in a first operating mode, at 1112. The first operating mode is associated with a first drive voltage. For example, controller 260 operates pump 150, reduced-pressure source 278, positive-pressure source 279, or a combination thereof, in first operating mode 297.

Method 1100 includes receiving, from a pressure sensor, pressure data indicating a pressure applied by the pump, at 1114. For example, controller 260 receives pressure data from first pressure sensor 272, second pressure sensor 274, or both.

Method 1100 also includes, responsive to determining that the pressure satisfies the first pressure threshold, operating the pump in a second operating mode, at 1116. The second operating mode is associated with a second drive voltage and a first duty cycle range, and the first drive voltage is greater than the second drive voltage. For example, if the pressure satisfies (e.g., is greater than or equal to) the first pressure threshold, controller 260 transitions pump 150 to second operating mode 298.

Method 1100 includes determining whether a battery level of one or more batteries of the wound therapy device satisfies a battery threshold or whether a leak counter satisfies a leak threshold, at 1118. For example, controller 260 determines whether a battery level of one or more batteries of device 210 satisfies a battery level threshold and/or whether leak counter 291 satisfies a leak counter threshold.

Method 1100 further includes, responsive to determining that the battery level fails to satisfy the battery threshold or that the leak counter satisfies the leak threshold, operating the pump in a third operating mode, at 1120. The third operating mode is associated with a second duty cycle range that is less than the first duty cycle range. For example, if the battery level fails to satisfy the battery threshold or if leak counter 291 satisfies the leak threshold, controller 260 transitions pump 150 to third operating mode 299.

Thus, method 1100 describes operating a pump in multiple different operating modes. The multiple operating modes provide benefits as compared to conventional pumps that operate in a single operating mode. For example, operating in the first operating mode may enable the pump to more quickly output a therapeutic amount of pressure. As another example, operating in the third operating mode may provide a lesser amount, but still a therapeutic amount, of pressure from the pump while extending the battery life of the wound therapy device.

One or more of the methods 400-1100 of FIGS. 4-11 may be implemented in a computer-readable storage device storing instructions that, when executed by a processor, cause the processor to perform the operations of the corresponding method.

It is noted that one or more operations described with reference to one of the methods of FIGS. 4-11 may be combined with one or more operations of another of FIGS. 4-11. For example, one or more operations of method 1000 may be combined with one or more operations of method 1100. Additionally, or alternatively, one or more operations described above with reference to FIGS. 1-3 may be combined with one or more operations of FIGS. 4-11, or a combination of FIGS. 4-11.

The above specification and examples provide a complete description of the structure and use of illustrative examples. Although certain aspects have been described above with a certain degree of particularity, or with reference to one or more individual examples, those skilled in the art could make numerous alterations to aspects of the present disclosure without departing from the scope of the present disclosure. As such, the various illustrative examples of the methods and systems are not intended to be limited to the particular forms disclosed. Rather, they include all modifications and alternatives falling within the scope of the claims, and implementations other than the ones shown may include some or all of the features of the depicted examples. For example, elements may be omitted or combined as a unitary structure, connections may be substituted, or both. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one example or may relate to several examples. Accordingly, no single implementation described herein should be construed as limiting and implementations of the disclosure may be suitably combined without departing from the teachings of the disclosure.

The previous description of the disclosed implementations is provided to enable a person skilled in the art to make or use the disclosed implementations. Various modifications to these implementations will be readily apparent to those skilled in the art, and the principles defined herein may be applied to other implementations without departing from the scope of the disclosure. Thus, the present disclosure is not intended to be limited to the implementations shown herein but is to be accorded the widest scope possible consistent with the principles and novel features as defined by the following claims. The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A wound therapy device comprising:
a battery;
a pump including at least four operating modes, the pump configured to be worn by a user; and
a controller coupled to the pump and configured to transition the pump from operating in a first operating mode to operating in a second operating mode responsive to a pressure of the wound therapy device satisfying a first pressure threshold and to transition the pump from operating in the second operating mode to a third operating mode or a fourth operating mode responsive to a condition being satisfied, wherein
the first operating mode is associated with a first drive voltage that is greater than a second drive voltage associated with the second operating mode,
the third operating mode delivers a first therapeutic amount of pressure from the pump, the first therapeutic amount of pressure being less than a second therapeutic amount of pressure delivered by the pump in the second operating mode,
the fourth operating mode delivers a third therapeutic amount of pressure from the pump, the third therapeutic amount of pressure being less than the second therapeutic amount of pressure delivered by the pump in the second operating mode, the fourth operating mode being activated in response to the condition being satisfied when a battery level of the battery fails to satisfy a battery threshold,
the fourth operating mode is associated with a third drive voltage that is less than the second drive voltage; and
the first therapeutic amount of pressure, the second therapeutic amount of pressure, and the third therapeutic amount of pressure are non-zero amounts of pressure.

2. The wound therapy device of claim 1, further comprising a pressure sensor coupled to the pump and configured to measure a pressure output by the pump and to send pressure data to the controller, the pressure data indicative of the pressure.

3. The wound therapy device of claim 1, further comprising a pressure sensor coupled to a dressing configured to be coupled to a wound site, the pressure sensor configured to measure the pressure at the dressing and to send pressure data to the controller, the pressure data indicative of the pressure.

4. The wound therapy device of claim 1, wherein the controller is further configured to:
responsive to the pressure failing to satisfy the first pressure threshold, determine whether a time elapsed since entering the first operating mode satisfies a time threshold; and
responsive to the time failing to satisfy the time threshold, continue to operate the pump in the first operating mode.

5. The wound therapy device of claim 4, wherein the controller is further configured to: responsive to the time satisfying the time threshold, increment a leak counter; determine whether the leak counter satisfies a leak threshold; and responsive to determining that the leak counter satisfies the leak threshold:
initiate a leak alert; and
operate the pump in the third operating mode, wherein the second operating mode is associated with a first duty cycle range of the pump, and wherein the third operating mode is associated with a second duty cycle range of the pump that is different from the first duty cycle range,
wherein the leak counter satisfying the leak threshold is the condition being satisfied.

6. The wound therapy device of claim 5, wherein:
the pump comprises one or more indicators; and
initiating the leak alert comprises activating one of the one or more indicators.

7. The wound therapy device of claim 5, wherein the controller is configured to initiate the leak alert by initiating transmission of a leak alert message to a mobile device associated with the user.

8. The wound therapy device of claim 5, wherein the controller is further configured to:
responsive to determining that the leak counter fails to satisfy the leak threshold, determine whether the battery level of the battery satisfies the battery threshold; and
responsive to determining that the battery level satisfies the battery threshold, continue to operate the pump in the first operating mode.

9. The wound therapy device of claim 8, wherein the controller is further configured to: responsive to determining that the battery level fails to satisfy the battery threshold:
initiate a low battery alert; and
operate the pump in the fourth operating mode, wherein the second operating mode is associated with a first duty cycle range, and wherein the fourth operating mode is associated with a third duty cycle range that is different from the first duty cycle range.

10. The wound therapy device of claim 9, wherein:
the pump comprises one or more indicators; and
initiating the low battery alert comprises activating one of the one or more indicators.

11. The wound therapy device of claim 9, wherein the controller is configured to initiate the low battery alert by initiating transmission of a low battery alert message to a mobile device associated with the user.

12. A method for providing wound therapy, the method comprising:
identifying a power-on event of a wound therapy device, the wound therapy device configured to be worn by a user;
responsive to the power-on event, operating a pump of the wound therapy device in a first operating mode, the pump including at least four operating modes and the first operating mode being associated with a first drive voltage;
receiving, from a pressure sensor of the wound therapy device, pressure data indicating a pressure applied by the pump;
determining whether the pressure satisfies a first pressure threshold;
responsive to determining that the pressure satisfies the first pressure threshold, operating the pump in a second operating mode, the second operating mode associated with a second drive voltage, wherein the first drive voltage is greater than the second drive voltage;

determining whether the wound therapy device satisfies a condition; and responsive to determining that the wound therapy device satisfies the condition, operating the pump in a third operating mode or a fourth operating mode, the third operating mode delivering a first therapeutic amount of pressure from the pump and the fourth operating mode delivering a third therapeutic amount of pressure from the pump, the first therapeutic amount of pressure and the third therapeutic amount of pressure being less than a second therapeutic amount of pressure delivered by the pump in the second operating mode, wherein the fourth operating mode is activated in response to the condition being satisfied when a battery level of a battery of the wound therapy device fails to satisfy a battery threshold, the fourth operating mode is associated with a third drive voltage that is less than the second drive voltage, and the first therapeutic amount of pressure, the second therapeutic amount of pressure, and the third therapeutic amount of pressure are non-zero amounts of pressure.

13. The method of claim 12, further comprising:
receiving, from the pressure sensor, second pressure data indicating a second pressure applied by the pump;
comparing the second pressure to a second pressure threshold; and
responsive to determining that the second pressure is greater than the second pressure threshold, reducing a duty cycle of the pump.

14. The method of claim 13, further comprising:
determining whether the battery level of the wound therapy device satisfies the battery threshold; and
responsive to the battery level satisfying the battery threshold, continuing to operate the pump in the second operating mode.

15. The method of claim 14, further comprising, responsive to the battery level failing to satisfy the battery threshold:
initiating a low battery alert; and
operating the pump in the fourth operating mode, wherein the second operating mode is associated with a first duty cycle range of the pump, and wherein the fourth operating mode is associated with a third duty cycle range of the pump that is different from the first duty cycle range.

16. The method of claim 13, further comprising:
responsive to determining that the second pressure is less than the second pressure threshold, determining whether a time since entering the second operating mode satisfies a time threshold; and
responsive to determining that the time does not satisfy the time threshold, increasing a duty cycle of the pump.

17. The method of claim 16, further comprising:
responsive to determining that the time satisfies the time threshold, incrementing a leak counter; and determining whether the leak counter satisfies a leak threshold.

18. The method of claim 17, further comprising:
responsive to determining that the leak counter does not satisfy the leak threshold, increasing the duty cycle of the pump; and
continuing to operate the pump in the second operating mode.

19. The method of claim 17, further comprising, responsive to determining that the leak counter satisfies the leak threshold:
initiating a leak alert; and
operating the pump in the third operating mode, wherein the second operating mode is associated with a first duty cycle range of the pump, and wherein the third operating mode is associated with a second duty cycle range of the pump that is different from the first duty cycle range,
wherein the leak counter satisfying the leak threshold is the condition being satisfied.

20. A wound therapy device comprising:
a battery;
a pump configured to be worn by a user; and
a controller coupled to the pump and configured to operate the pump in one of at least four operating modes, wherein a first operating mode of the at least four operating modes is associated with a first drive voltage, wherein a second operating mode of the at least four operating modes is associated with a second drive voltage and a first duty cycle range of the pump, the second drive voltage less than the first drive voltage, and wherein a third operating mode of the at least four operating modes is associated with a second duty cycle range of the pump, the second duty cycle range different from the first duty cycle range, wherein
the third operating mode delivers a first therapeutic amount of pressure from the pump, the first therapeutic amount of pressure being less than a second therapeutic amount of pressure delivered by the pump in the second operating mode,
a fourth operating mode of the at least four operating modes delivers a third therapeutic amount of pressure from the pump, the third therapeutic amount of pressure being less than the second therapeutic amount of pressure delivered by the pump in the second operating mode, the fourth operating mode being activated in response to a battery level of the battery failing to satisfy a battery threshold,
the fourth operating mode is associated with a third drive voltage that is less than the second drive voltage; and
the first therapeutic amount of pressure, the second therapeutic amount of pressure, and the third therapeutic amount of pressure are non-zero amounts of pressure.

* * * * *